United States Patent
Quadri et al.

(10) Patent No.: US 10,166,097 B2
(45) Date of Patent: Jan. 1, 2019

(54) REPLACEMENT HEART VALVE AND METHOD

(71) Applicant: Edwards Lifesciences CardiAQ LLC, Irvine, CA (US)

(72) Inventors: Arshad Quadri, West Hartford, CT (US); J. Brent Ratz, Winchester, MA (US); Robrecht Michiels, Laguna Hills, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 116 days.

(21) Appl. No.: 15/011,247

(22) Filed: Jan. 29, 2016

(65) Prior Publication Data
US 2016/0143733 A1    May 26, 2016

Related U.S. Application Data

(63) Continuation of application No. 13/755,406, filed on Jan. 31, 2013, now Pat. No. 9,480,560, which is a
(Continued)

(51) Int. Cl.
*A61F 2/24* (2006.01)

(52) U.S. Cl.
CPC .......... *A61F 2/2418* (2013.01); *A61F 2/2427* (2013.01); *A61F 2/24* (2013.01); *A61F 2/2412* (2013.01); *A61F 2/2439* (2013.01); *A61F 2210/0014* (2013.01); *A61F 2210/0076* (2013.01); *A61F 2220/005* (2013.01); *A61F 2220/0008* (2013.01); *A61F 2220/0016* (2013.01); *A61F 2220/0058* (2013.01);
(Continued)

(58) Field of Classification Search
CPC ...... A61F 2/07–2002/077; A61F 2/24–2/2475; A61F 2210/0076; A61F 2250/0039
See application file for complete search history.

(56) References Cited

U.S. PATENT DOCUMENTS

| | | |
|---|---|---|
| 865,203 A | 9/1907 | Mustonen et al. |
| 3,657,744 A | 4/1972 | Ersek |

(Continued)

FOREIGN PATENT DOCUMENTS

| | | |
|---|---|---|
| CA | 2304325 A1 | 10/2000 |
| CA | 2 827 556 A1 | 7/2012 |

(Continued)

OTHER PUBLICATIONS

US 8,062,357, 11/2011, Salahieh et al. (withdrawn)
(Continued)

*Primary Examiner* — Yashita Sharma
*Assistant Examiner* — Rebecca Preston
(74) *Attorney, Agent, or Firm* — Knobbe, Martens, Olson & Bear LLP; Joel B. German; AnneMarie Kaiser

(57) ABSTRACT

A replacement heart valve has an expandable frame configured to engage a native valve annulus and a valve body mounted to the expandable frame. The valve body can have a plurality of valve leaflets configured to open to allow flow in a first direction and engage one another so as to close and prevent flow in a second direction, the second direction being opposite the first direction.

17 Claims, 9 Drawing Sheets

Related U.S. Application Data continuation of application No. 13/403,929, filed on Feb. 23, 2012, now Pat. No. 9,730,790.

(60) Provisional application No. 61/445,963, filed on Feb. 23, 2011.

(52) U.S. Cl.
CPC .............. A61F 2220/0075 (2013.01); A61F 2230/0054 (2013.01); A61F 2250/006 (2013.01); A61F 2250/0039 (2013.01); A61F 2250/0069 (2013.01); A61F 2250/0071 (2013.01)

(56) References Cited

U.S. PATENT DOCUMENTS

| | | |
|---|---|---|
| 3,671,979 A | 6/1972 | Moulopoulos |
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,994,077 A | 2/1991 | Dobben |
| 5,197,978 A | 3/1993 | Hess |
| 5,326,371 A | 7/1994 | Love et al. |
| 5,332,402 A | 7/1994 | Teitelbaum |
| 5,370,685 A | 12/1994 | Stevens |
| 5,397,355 A | 3/1995 | Marin |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,509,930 A | 4/1996 | Love |
| 5,545,214 A | 8/1996 | Stevens |
| 5,554,185 A | 9/1996 | Block et al. |
| 5,575,818 A | 11/1996 | Pinchuk |
| 5,607,444 A | 3/1997 | Lam |
| 5,607,469 A | 3/1997 | Frey |
| 5,669,919 A | 9/1997 | Sanders et al. |
| 5,693,061 A | 12/1997 | Pierce et al. |
| 5,697,382 A | 12/1997 | Love et al. |
| D390,957 S | 2/1998 | Fontaine |
| 5,713,952 A | 2/1998 | Vanney et al. |
| 5,725,519 A | 3/1998 | Penner |
| 5,769,812 A | 6/1998 | Stevens et al. |
| 5,807,398 A | 9/1998 | Shaknovich |
| 5,810,873 A | 9/1998 | Morales |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,876,437 A | 3/1999 | Vanney et al. |
| 5,879,381 A | 3/1999 | Moriuch et al. |
| 5,902,334 A | 5/1999 | Dwyer et al. |
| 5,935,108 A | 8/1999 | Katoh |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt |
| 6,168,614 B1 | 1/2001 | Andersen et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,425,916 B1 | 7/2002 | Garrison et al. |
| 6,440,164 B1 | 8/2002 | DiMatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,517,550 B1 | 2/2003 | Kónya et al. |
| 6,517,573 B1 | 2/2003 | Pollock |
| 6,527,800 B1 | 3/2003 | McGuckin, Jr. et al. |
| 6,582,462 B1 | 6/2003 | Andersen et al. |
| 6,602,281 B1 | 8/2003 | Klein |
| 6,610,088 B1 | 8/2003 | Gabbay |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin et al. |
| 6,682,537 B2 | 1/2004 | Ouriel et al. |
| 6,695,878 B2 | 2/2004 | McGuckin et al. |
| 6,712,836 B1 | 3/2004 | Berg et al. |
| 6,723,123 B1 | 4/2004 | Kazatchkov et al. |
| 6,730,118 B2 | 5/2004 | Spenser et al. |
| 6,733,523 B2 | 5/2004 | Shaolian et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,477 B2 | 6/2005 | McGuckin, Jr. et al. |
| 6,908,481 B2 | 6/2005 | Cribier |
| 6,929,660 B1 | 8/2005 | Ainsworth et al. |
| 6,936,058 B2 | 8/2005 | Forde et al. |
| 6,926,732 B2 | 9/2005 | Derus et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,962 B2 | 5/2006 | Elliott |
| 7,044,966 B2 | 5/2006 | Svanidze et al. |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,153,322 B2 | 12/2006 | Alt |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| 7,252,682 B2 | 8/2007 | Seguin |
| D553,747 S | 10/2007 | Fliedner |
| 7,276,078 B2 | 10/2007 | Spenser et al. |
| 7,276,084 B2 | 10/2007 | Yang et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,585,321 B2 | 9/2009 | Cribier |
| 7,608,114 B2 | 10/2009 | Levine et al. |

(56) References Cited

U.S. PATENT DOCUMENTS

| | | |
|---|---|---|
| 7,615,072 B2 | 11/2009 | Rust et al. |
| 7,618,446 B2 | 11/2009 | Andersen et al. |
| 7,628,805 B2 | 12/2009 | Spenser et al. |
| 7,632,298 B2 | 12/2009 | Hijlkema et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,771,472 B2 | 8/2010 | Hedricksen et al. |
| 7,785,360 B2 | 8/2010 | Freitag |
| 7,803,185 B2 | 9/2010 | Gabbay |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,846,203 B2 | 12/2010 | Cribier |
| 7,871,435 B2 | 1/2011 | Carpentier |
| 7,892,281 B2 | 2/2011 | Seguin et al. |
| D635,261 S | 3/2011 | Rossi |
| D635,262 S | 3/2011 | Rossi |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,016,870 B2 | 9/2011 | Chew et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,926 B2 | 5/2012 | Hartley et al. |
| 8,167,934 B2 | 5/2012 | Styrc et al. |
| 8,177,799 B2 | 5/2012 | Orban, III |
| 8,182,528 B2 | 5/2012 | Salahieh et al. |
| 8,182,530 B2 | 5/2012 | Huber |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| 8,221,493 B2 | 7/2012 | Boyle et al. |
| 8,226,710 B2 | 7/2012 | Nguyen et al. |
| D665,079 S | 8/2012 | Zago |
| D665,080 S | 8/2012 | Zago |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,361,137 B2 | 1/2013 | Perouse |
| 8,361,537 B2 | 1/2013 | Shanley |
| 8,398,708 B2 | 3/2013 | Meiri et al. |
| 8,403,983 B2 | 3/2013 | Quadri et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,466 B2 | 5/2013 | Duhay et al. |
| 8,449,599 B2 | 5/2013 | Chau et al. |
| 8,449,625 B2 | 5/2013 | Campbell et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,106 B2 | 8/2013 | Duffy et al. |
| 8,535,368 B2 | 9/2013 | Headley, Jr. et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,584,849 B2 | 11/2013 | McCaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,623,075 B2 | 1/2014 | Murray, III et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,203 B2 | 2/2014 | Quadri et al. |
| 8,668,730 B2 | 3/2014 | McGuckin, Jr. et al. |
| 8,668,733 B2 | 3/2014 | Haug et al. |
| 8,672,992 B2 | 3/2014 | Orr |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,707,957 B2 | 4/2014 | Callister et al. |
| 8,718,765 B2 | 5/2014 | Baumann et al. |
| 8,721,707 B2 | 5/2014 | Boucher et al. |
| 8,721,708 B2 | 5/2014 | Sequin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,758,432 B2 | 6/2014 | Solem |
| 8,764,814 B2 | 7/2014 | Solem |
| 8,764,818 B2 | 7/2014 | Gregg |
| 8,764,820 B2 | 7/2014 | Dehdashtian et al. |
| 8,771,344 B2 | 7/2014 | Tran et al. |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,778,020 B2 | 7/2014 | Gregg et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,790,396 B2 | 7/2014 | Bergheim et al. |
| 8,795,356 B2 | 8/2014 | Quadri et al. |
| 8,795,357 B2 | 8/2014 | Yohanan et al. |
| 8,798,771 B2 | 8/2014 | Casset et al. |
| 8,821,569 B2 | 9/2014 | Gurskis et al. |
| 8,828,078 B2 | 9/2014 | Salahieh et al. |
| 8,828,079 B2 | 9/2014 | Thielen et al. |
| 8,834,349 B2 | 9/2014 | Waisblatt et al. |
| 8,834,563 B2 | 9/2014 | Righini |
| 8,834,564 B2 | 9/2014 | Tuval et al. |
| 8,844,365 B2 | 9/2014 | Gregg et al. |
| 8,845,718 B2 | 9/2014 | Tuval et al. |
| 8,852,267 B2 | 10/2014 | Cattaneo |

(56) References Cited

U.S. PATENT DOCUMENTS

| | | |
|---|---|---|
| 8,870,947 B2 | 10/2014 | Shaw |
| 8,870,948 B1 | 10/2014 | Erzberger et al. |
| 8,876,883 B2 | 11/2014 | Rust |
| 8,876,893 B2 | 11/2014 | Dwork et al. |
| 8,876,895 B2 | 11/2014 | Tuval et al. |
| 8,888,709 B2 | 11/2014 | Shuros et al. |
| 8,888,730 B2 | 11/2014 | Rossi et al. |
| 8,894,702 B2 | 11/2014 | Quadri et al. |
| 8,911,455 B2 | 12/2014 | Quadri et al. |
| 8,911,490 B2 | 12/2014 | Perkins et al. |
| 8,923,963 B2 | 12/2014 | Bonner et al. |
| 8,926,688 B2 | 1/2015 | Burkart et al. |
| 8,926,690 B2 | 1/2015 | Kovalsky |
| 8,926,693 B2 | 1/2015 | Duffy et al. |
| 8,926,694 B2 | 1/2015 | Costello |
| 8,945,209 B2 | 2/2015 | Bonyuet et al. |
| 8,951,299 B2 | 2/2015 | Paul et al. |
| 8,956,405 B2 | 2/2015 | Wang et al. |
| 8,961,583 B2 | 2/2015 | Hojeibane et al. |
| 8,961,593 B2 | 2/2015 | Bonhoeffer et al. |
| 8,961,594 B2 | 2/2015 | Maisano et al. |
| 8,961,595 B2 | 2/2015 | Alkhatib |
| 8,968,336 B2 | 3/2015 | Conklin et al. |
| 8,974,524 B2 | 3/2015 | Yeung et al. |
| 8,979,922 B2 | 3/2015 | Jayasinghe et al. |
| 8,986,371 B2 | 3/2015 | Quill et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,992,761 B2 | 3/2015 | Lin |
| 8,998,979 B2 | 4/2015 | Seguin et al. |
| 8,998,980 B2 | 4/2015 | Shipley et al. |
| 9,005,270 B2 | 4/2015 | Perkins et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,023,100 B2 | 5/2015 | Quadri et al. |
| 9,028,545 B2 | 5/2015 | Taylor |
| 9,029,418 B2 | 5/2015 | Dove et al. |
| 9,033,887 B2 | 5/2015 | Ionasec et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 2001/0007956 A1 | 7/2001 | Letac et al. |
| 2001/0021872 A1 | 9/2001 | Bailey et al. |
| 2001/0047180 A1 | 11/2001 | Grudem et al. |
| 2001/0047200 A1 | 11/2001 | White |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0055772 A1 | 5/2002 | McGuckin et al. |
| 2002/0111619 A1 | 8/2002 | Keast et al. |
| 2002/0183827 A1 | 12/2002 | Derus et al. |
| 2003/0040792 A1 | 2/2003 | Gabbay |
| 2003/0105517 A1 | 6/2003 | White et al. |
| 2003/0114913 A1 | 6/2003 | Spenser et al. |
| 2003/0120263 A1 | 6/2003 | Ouriel et al. |
| 2003/0120330 A1 | 6/2003 | Ouriel et al. |
| 2003/0120333 A1 | 6/2003 | Ouriel et al. |
| 2003/0130729 A1 | 7/2003 | Paniagua |
| 2003/0149477 A1 | 8/2003 | Gabbay |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093058 A1 | 5/2004 | Cottone et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0133273 A1 | 7/2004 | Cox |
| 2004/0186561 A1 | 9/2004 | McGuckin, Jr. et al. |
| 2004/0193261 A1 | 9/2004 | Berreklou |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225352 A1* | 11/2004 | Osborne .............. A61F 2/2418 623/1.24 |
| 2004/0225353 A1 | 11/2004 | McGuckin, Jr. et al. |
| 2004/0236411 A1 | 11/2004 | Sarac et al. |
| 2004/0243230 A1 | 12/2004 | Navia et al. |
| 2004/0249433 A1 | 12/2004 | Freitag |
| 2005/0033398 A1 | 2/2005 | Seguin |
| 2005/0038470 A1 | 2/2005 | van der Burg et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0119722 A1 | 6/2005 | Styrc et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug et al. |
| 2005/0137695 A1 | 6/2005 | Salahieh et al. |
| 2005/0137701 A1 | 6/2005 | Salahieh et al. |
| 2005/0159811 A1 | 6/2005 | Lane |
| 2005/0154444 A1 | 7/2005 | Quadri |
| 2005/0182483 A1 | 8/2005 | Osborne et al. |
| 2005/0182486 A1 | 8/2005 | Gabbay |
| 2005/0203616 A1 | 9/2005 | Cribier |
| 2005/0216079 A1 | 9/2005 | Macoviak |
| 2005/0234546 A1 | 10/2005 | Nugent et al. |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0106454 A1* | 5/2006 | Osborne .............. A61F 2/2418 623/1.24 |
| 2006/0116625 A1 | 6/2006 | Renati et al. |
| 2006/0129235 A1 | 6/2006 | Seguin et al. |
| 2006/0149360 A1 | 7/2006 | Schwammenthal et al. |
| 2006/0161265 A1 | 7/2006 | Levine et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0010876 A1 | 1/2007 | Salahieh et al. |
| 2007/0016286 A1 | 1/2007 | Herrmann et al. |
| 2007/0043435 A1 | 2/2007 | Seguin et al. |
| 2007/0050021 A1 | 3/2007 | Johnson |
| 2007/0067016 A1 | 3/2007 | Jung |
| 2007/0100432 A1 | 5/2007 | Case et al. |
| 2007/0118206 A1 | 5/2007 | Colgan et al. |
| 2007/0118207 A1 | 5/2007 | Amplatz et al. |
| 2007/0123798 A1 | 5/2007 | Rahamimov |
| 2007/0129794 A1 | 6/2007 | Realyvasquez |
| 2007/0142906 A1 | 6/2007 | Figulla et al. |
| 2007/0162107 A1 | 7/2007 | Haug et al. |
| 2007/0168022 A1* | 7/2007 | Eldridge .............. A61F 2/2409 623/2.4 |
| 2007/0185559 A1 | 8/2007 | Shelso |

(56) References Cited

U.S. PATENT DOCUMENTS

| | | |
|---|---|---|
| 2007/0213813 A1 | 9/2007 | Von Segesser et al. |
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0270932 A1 | 11/2007 | Headley et al. |
| 2007/0270937 A1 | 11/2007 | Leanna |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071361 A1 | 3/2008 | Tuval et al. |
| 2008/0071363 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0087581 A1 | 4/2008 | Shanley |
| 2008/0097571 A1 | 4/2008 | Denison et al. |
| 2008/0097595 A1* | 4/2008 | Gabbay ............... A61B 17/3417 623/2.42 |
| 2008/0114441 A1 | 5/2008 | Rust et al. |
| 2008/0125853 A1 | 5/2008 | Boyle et al. |
| 2008/0125859 A1 | 5/2008 | Salahieh et al. |
| 2008/0133003 A1 | 6/2008 | Seguin |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208307 A1 | 8/2008 | Ben-Muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0243233 A1 | 10/2008 | Ben-Muvhar et al. |
| 2008/0243245 A1 | 10/2008 | Thambar et al. |
| 2008/0262596 A1 | 10/2008 | Xiao |
| 2008/0269878 A1 | 10/2008 | Lobbi |
| 2008/0275549 A1 | 11/2008 | Rowe |
| 2009/0005863 A1 | 1/2009 | Goetz et al. |
| 2009/0054976 A1 | 2/2009 | Tuval et al. |
| 2009/0062908 A1 | 3/2009 | Bonhoeffer et al. |
| 2009/0076585 A1 | 3/2009 | Hendriksen |
| 2009/0076598 A1 | 3/2009 | Salahieh et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0125096 A1 | 5/2009 | Chu et al. |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf et al. |
| 2009/0171438 A1 | 7/2009 | Chuter et al. |
| 2009/0171456 A1 | 7/2009 | Kveen et al. |
| 2009/0177262 A1 | 7/2009 | Oberti et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0192601 A1 | 7/2009 | Rafiee et al. |
| 2009/0216314 A1 | 8/2009 | Quadri |
| 2009/0234443 A1 | 9/2009 | Ottma et al. |
| 2009/0248132 A1 | 10/2009 | Bloom et al. |
| 2009/0248133 A1 | 10/2009 | Bloom et al. |
| 2009/0264997 A1 | 10/2009 | Salahieh et al. |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2010/0004740 A1 | 1/2010 | Sequin et al. |
| 2010/0036479 A1 | 2/2010 | Hill et al. |
| 2010/0049306 A1 | 2/2010 | House et al. |
| 2010/0082094 A1 | 4/2010 | Quadri |
| 2010/0094411 A1 | 4/2010 | Tuval et al. |
| 2010/0114299 A1 | 5/2010 | Ben Muvhar et al. |
| 2010/0114305 A1 | 5/2010 | Kang et al. |
| 2010/0121461 A1 | 5/2010 | Sobrino-Serrano et al. |
| 2010/0161027 A1 | 6/2010 | Orr |
| 2010/0179633 A1 | 7/2010 | Solem |
| 2010/0179647 A1 | 7/2010 | Carpenter et al. |
| 2010/0191326 A1 | 7/2010 | Alkhatib |
| 2010/0217382 A1 | 8/2010 | Chau et al. |
| 2010/0249894 A1 | 9/2010 | Chau et al. |
| 2010/0249908 A1 | 9/2010 | Chau et al. |
| 2010/0249911 A1 | 9/2010 | Alkhatib |
| 2010/0256723 A1 | 10/2010 | Murray |
| 2010/0262157 A1 | 10/2010 | Silver et al. |
| 2010/0274345 A1 | 10/2010 | Rust |
| 2010/0280606 A1 | 11/2010 | Naor |
| 2010/0298931 A1 | 11/2010 | Quadri et al. |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0022157 A1 | 1/2011 | Essinger et al. |
| 2011/0022165 A1 | 1/2011 | Oba et al. |
| 2011/0029067 A1 | 2/2011 | McGuckin, Jr. et al. |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0208297 A1 | 8/2011 | Tuval et al. |
| 2011/0208298 A1 | 8/2011 | Tuval et al. |
| 2011/0218619 A1 | 9/2011 | Benichou et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2011/0319989 A1 | 12/2011 | Lane et al. |
| 2012/0016411 A1 | 1/2012 | Tuval |
| 2012/0022639 A1 | 1/2012 | Hacohen et al. |
| 2012/0041550 A1 | 2/2012 | Salahieh et al. |
| 2012/0059452 A1 | 3/2012 | Boucher et al. |
| 2012/0059454 A1 | 3/2012 | Millwee et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0179239 A1 | 7/2012 | Quadri et al. |
| 2012/0215303 A1 | 8/2012 | Quadri et al. |
| 2012/0259405 A1 | 10/2012 | Weber et al. |
| 2012/0271398 A1 | 10/2012 | Essinger et al. |
| 2012/0283824 A1 | 11/2012 | Lutter et al. |
| 2012/0290062 A1 | 11/2012 | McNamara et al. |
| 2012/0296418 A1 | 11/2012 | Bonyuet et al. |
| 2012/0303116 A1 | 11/2012 | Gorman, III et al. |
| 2012/0310328 A1 | 12/2012 | Olson et al. |
| 2012/0323316 A1 | 12/2012 | Chau et al. |
| 2013/0006294 A1 | 1/2013 | Kashkarov |
| 2013/0018458 A1 | 1/2013 | Yohanan et al. |
| 2013/0053950 A1 | 2/2013 | Rowe et al. |
| 2013/0090727 A1 | 4/2013 | Forster et al. |
| 2013/0110227 A1 | 5/2013 | Quadri et al. |
| 2013/0131788 A1 | 5/2013 | Quadri et al. |
| 2013/0131793 A1 | 5/2013 | Quadri et al. |
| 2013/0138203 A1 | 5/2013 | Quadri et al. |
| 2013/0138207 A1 | 5/2013 | Quadri et al. |
| 2013/0144375 A1 | 6/2013 | Giasolli et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0150956 A1 | 6/2013 | Yohanan et al. |
| 2013/0158600 A1 | 6/2013 | Conklin et al. |
| 2013/0172983 A1 | 7/2013 | Clerc et al. |
| 2013/0184811 A1 | 7/2013 | Rowe et al. |
| 2013/0184813 A1 | 7/2013 | Quadri et al. |
| 2013/0190861 A1 | 7/2013 | Chau et al. |
| 2013/0190862 A1 | 7/2013 | Pintor et al. |
| 2013/0211508 A1 | 8/2013 | Lane et al. |
| 2013/0211513 A1 | 8/2013 | Rourke et al. |
| 2013/0238072 A1 | 9/2013 | Deterre et al. |

(56) References Cited

U.S. PATENT DOCUMENTS

| | | |
|---|---|---|
| 2013/0238073 A1 | 9/2013 | Makdissi et al. |
| 2013/0245615 A1 | 9/2013 | Koltz |
| 2013/0253570 A1 | 9/2013 | Bates |
| 2013/0253571 A1 | 9/2013 | Bates |
| 2013/0253635 A1 | 9/2013 | Straubinger et al. |
| 2013/0253642 A1 | 9/2013 | Brecker |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261740 A1 | 10/2013 | Eberhardt et al. |
| 2013/0261742 A1 | 10/2013 | Gaschino et al. |
| 2013/0268064 A1 | 10/2013 | Duffy |
| 2013/0268065 A1 | 10/2013 | Costello et al. |
| 2013/0268068 A1 | 10/2013 | Marchisio et al. |
| 2013/0272994 A1 | 10/2013 | Fu et al. |
| 2013/0274855 A1 | 10/2013 | Stante et al. |
| 2013/0274873 A1 | 10/2013 | Delaloye et al. |
| 2013/0281979 A1 | 10/2013 | Arnim et al. |
| 2013/0282028 A1 | 10/2013 | Conklin et al. |
| 2013/0282113 A1 | 10/2013 | Punga et al. |
| 2013/0282114 A1 | 10/2013 | Schweich, Jr. et al. |
| 2013/0304196 A1 | 11/2013 | Kelly |
| 2013/0304197 A1 | 11/2013 | Buchbinder et al. |
| 2013/0304199 A1 | 11/2013 | Sutton et al. |
| 2013/0304200 A1 | 11/2013 | McLean et al. |
| 2013/0310928 A1 | 11/2013 | Morriss et al. |
| 2013/0323302 A1 | 12/2013 | Constable et al. |
| 2013/0324804 A1 | 12/2013 | McKeown et al. |
| 2013/0325110 A1 | 12/2013 | Khalil et al. |
| 2013/0325111 A1 | 12/2013 | Campbell et al. |
| 2013/0325116 A1 | 12/2013 | Sundler et al. |
| 2013/0331929 A1 | 12/2013 | Mitra et al. |
| 2013/0331931 A1 | 12/2013 | Gregg et al. |
| 2013/0338698 A1 | 12/2013 | Flanagan |
| 2013/0338763 A1 | 12/2013 | Rowe et al. |
| 2013/0338766 A1 | 12/2013 | Hastings et al. |
| 2013/0345786 A1 | 12/2013 | Behan |
| 2014/0005764 A1 | 1/2014 | Schroeder |
| 2014/0005772 A1 | 1/2014 | Edelman et al. |
| 2014/0014530 A1 | 1/2014 | Lin |
| 2014/0018911 A1 | 1/2014 | Zhou et al. |
| 2014/0018912 A1 | 1/2014 | Delaloye et al. |
| 2014/0025087 A1 | 1/2014 | Richardson |
| 2014/0031857 A1 | 1/2014 | Richardson |
| 2014/0031864 A1 | 1/2014 | Jafari et al. |
| 2014/0031922 A1 | 1/2014 | Duffy et al. |
| 2014/0031923 A1 | 1/2014 | Rogers et al. |
| 2014/0039609 A1 | 2/2014 | Campbell et al. |
| 2014/0039611 A1 | 2/2014 | Lane et al. |
| 2014/0046353 A1 | 2/2014 | Adams |
| 2014/0046427 A1 | 2/2014 | Michalak |
| 2014/0046433 A1 | 2/2014 | Kovalsky |
| 2014/0046434 A1 | 2/2014 | Rolando et al. |
| 2014/0052170 A1 | 2/2014 | Heuser et al. |
| 2014/0052237 A1 | 2/2014 | Lane et al. |
| 2014/0052242 A1 | 2/2014 | Revuelta et al. |
| 2014/0067048 A1 | 3/2014 | Chau et al. |
| 2014/0067049 A1 | 3/2014 | Costello |
| 2014/0067050 A1 | 3/2014 | Costello et al. |
| 2014/0067052 A1 | 3/2014 | Chau et al. |
| 2014/0067054 A1 | 3/2014 | Chau et al. |
| 2014/0088680 A1 | 3/2014 | Costello et al. |
| 2014/0088685 A1 | 3/2014 | Yevzlin et al. |
| 2014/0088692 A1 | 3/2014 | Wright |
| 2014/0088695 A1 | 3/2014 | Figulla et al. |
| 2014/0100597 A1 | 4/2014 | Wang et al. |
| 2014/0100651 A1 | 4/2014 | Kheradvar et al. |
| 2014/0100653 A1 | 4/2014 | Savage et al. |
| 2014/0110279 A1 | 4/2014 | Kruetzfeldt et al. |
| 2014/0114340 A1 | 4/2014 | Zhou et al. |
| 2014/0114345 A1 | 4/2014 | Ciobanu et al. |
| 2014/0114391 A1 | 4/2014 | Tabor |
| 2014/0114402 A1 | 4/2014 | Ahlberg et al. |
| 2014/0114408 A1 | 4/2014 | Dwork |
| 2014/0121719 A1 | 5/2014 | Bonner et al. |
| 2014/0121763 A1 | 5/2014 | Duffy et al. |
| 2014/0121764 A1 | 5/2014 | De Paulis et al. |
| 2014/0128726 A1 | 5/2014 | Quill et al. |
| 2014/0128963 A1 | 5/2014 | Quill et al. |
| 2014/0128964 A1 | 5/2014 | Delaloye |
| 2014/0134322 A1 | 5/2014 | Larsen et al. |
| 2014/0135908 A1 | 5/2014 | Glozman et al. |
| 2014/0135909 A1 | 5/2014 | Carr et al. |
| 2014/0142693 A1 | 5/2014 | Krivoruchko et al. |
| 2014/0142694 A1 | 5/2014 | Tabor et al. |
| 2014/0144000 A1 | 5/2014 | Creaven et al. |
| 2014/0148889 A1 | 5/2014 | Deshmukh et al. |
| 2014/0155990 A1 | 6/2014 | Nyuli et al. |
| 2014/0162563 A1 | 6/2014 | Mastrototaro |
| 2014/0163668 A1 | 6/2014 | Rafiee |
| 2014/0172083 A1 | 6/2014 | Bruchman et al. |
| 2014/0172085 A1 | 6/2014 | Quadri et al. |
| 2014/0172086 A1 | 6/2014 | Quadri et al. |
| 2014/0180337 A1 | 6/2014 | Miraki et al. |
| 2014/0188219 A1 | 7/2014 | Conklin et al. |
| 2014/0188221 A1 | 7/2014 | Chung et al. |
| 2014/0194975 A1 | 7/2014 | Quill et al. |
| 2014/0194981 A1 | 7/2014 | Menk et al. |
| 2014/0194982 A1 | 7/2014 | Kovalsky et al. |
| 2014/0194983 A1 | 7/2014 | Kovalsky et al. |
| 2014/0200457 A1 | 7/2014 | Shuros et al. |
| 2014/0200660 A1 | 7/2014 | Savage et al. |
| 2014/0213889 A1 | 7/2014 | Macht |
| 2014/0214069 A1 | 7/2014 | Franklin |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214159 A1 | 7/2014 | Vidlund et al. |
| 2014/0214160 A1 | 7/2014 | Naor |
| 2014/0215791 A1 | 8/2014 | Soundararajan et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0228945 A1 | 8/2014 | Valdez et al. |
| 2014/0230515 A1 | 8/2014 | Tuval et al. |
| 2014/0236287 A1 | 8/2014 | Clague et al. |
| 2014/0236288 A1 | 8/2014 | Lambrecht et al. |
| 2014/0243879 A1 | 8/2014 | Rothstein et al. |
| 2014/0243880 A1 | 8/2014 | Schotzko et al. |
| 2014/0243953 A1 | 8/2014 | Stante et al. |
| 2014/0243966 A1 | 8/2014 | Garde et al. |
| 2014/0257463 A1 | 9/2014 | Sweeney et al. |
| 2014/0257476 A1 | 9/2014 | Montorfano et al. |
| 2014/0260097 A1 | 9/2014 | Avery et al. |
| 2014/0277390 A1 | 9/2014 | Ratz et al. |
| 2014/0277402 A1 | 9/2014 | Essinger et al. |
| 2014/0277403 A1 | 9/2014 | Peter |
| 2014/0277408 A1 | 9/2014 | Folan |
| 2014/0277410 A1 | 9/2014 | Börtlein et al. |
| 2014/0277418 A1 | 9/2014 | Miller |
| 2014/0277419 A1 | 9/2014 | Garde et al. |
| 2014/0277422 A1 | 9/2014 | Ratz et al. |
| 2014/0277423 A1 | 9/2014 | Alkhatib et al. |
| 2014/0277427 A1 | 9/2014 | Ratz et al. |
| 2014/0288480 A1 | 9/2014 | Zimmerman et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330366 A1 | 11/2014 | Dehdashtian et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0331475 A1 | 11/2014 | Duffy et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |

(56) References Cited

U.S. PATENT DOCUMENTS

| | | |
|---|---|---|
| 2014/0350523 A1 | 11/2014 | Dehdashtian et al. |
| 2014/0350666 A1 | 11/2014 | Righini |
| 2014/0350668 A1 | 11/2014 | Delaloye et al. |
| 2014/0358221 A1 | 12/2014 | Ho et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371833 A1 | 12/2014 | Ghosh et al. |
| 2014/0371841 A1 | 12/2014 | Casley et al. |
| 2014/0371842 A1 | 12/2014 | Marquez et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005873 A1 | 1/2015 | Chang et al. |
| 2015/0012085 A1 | 1/2015 | Salahieh et al. |
| 2015/0018625 A1 | 1/2015 | Miraki et al. |
| 2015/0018879 A1 | 1/2015 | Moehle et al. |
| 2015/0018938 A1 | 1/2015 | Von Segesser et al. |
| 2015/0018939 A1 | 1/2015 | Colson et al. |
| 2015/0018944 A1 | 1/2015 | O'Connell et al. |
| 2015/0025621 A1 | 1/2015 | Costello et al. |
| 2015/0025622 A1 | 1/2015 | Creaven et al. |
| 2015/0025623 A1 | 1/2015 | Granada et al. |
| 2015/0026635 A1 | 1/2015 | Gohr et al. |
| 2015/0032153 A1 | 1/2015 | Quadri et al. |
| 2015/0032174 A1 | 1/2015 | Ghosh |
| 2015/0039081 A1 | 2/2015 | Costello |
| 2015/0039083 A1 | 2/2015 | Rafiee |
| 2015/0051698 A1 | 2/2015 | Ruyra Baliarda et al. |
| 2015/0066137 A1 | 3/2015 | Chen et al. |
| 2015/0066140 A1 | 3/2015 | Quadri |
| 2015/0073537 A1 | 3/2015 | Jimenez et al. |
| 2015/0081009 A1 | 3/2015 | Quadri |
| 2015/0081011 A1 | 3/2015 | Young et al. |
| 2015/0088245 A1 | 3/2015 | Costello |
| 2015/0088250 A1 | 3/2015 | Zeng et al. |
| 2015/0094803 A1 | 4/2015 | Navia |
| 2015/0100118 A1 | 4/2015 | Benton |
| 2015/0112430 A1 | 4/2015 | Creaven et al. |
| 2015/0119692 A1 | 4/2015 | McHenry et al. |
| 2015/0119974 A1 | 4/2015 | Rothstein et al. |
| 2015/0119980 A1 | 4/2015 | Beith et al. |
| 2015/0119982 A1 | 4/2015 | Quill et al. |
| 2015/0122687 A1 | 5/2015 | Zeng et al. |
| 2015/0127093 A1 | 5/2015 | Hosmer |
| 2015/0142103 A1 | 5/2015 | Vidlund |
| 2015/0148731 A1 | 5/2015 | McNamara et al. |
| 2015/0157458 A1 | 6/2015 | Thambar et al. |
| 2015/0196390 A1 | 7/2015 | Ma et al. |
| 2015/0196393 A1 | 7/2015 | Vidlund |
| 2015/0238315 A1 | 8/2015 | Rabito et al. |
| 2015/0305864 A1 | 10/2015 | Quadri et al. |

FOREIGN PATENT DOCUMENTS

| | | |
|---|---|---|
| DE | 3128704 | 2/1983 |
| DE | 10 2006 052 564 | 12/2007 |
| EP | 0 657 147 | 6/1995 |
| EP | 1 472 996 B1 | 11/2004 |
| EP | 1 255 510 B1 | 4/2007 |
| EP | 2 777 617 | 9/2014 |
| GB | 1 264 471 | 2/1972 |
| GB | 1315 844 | 5/1973 |
| GB | 2 245 495 | 1/1992 |
| GB | 2 398 245 | 8/2004 |
| JP | 2002-540889 | 12/2002 |
| JP | 2008-541865 | 11/2008 |
| WO | WO 1997/049355 | 12/1997 |
| WO | WO 2000/053104 | 9/2000 |
| WO | WO 2000/61034 | 10/2000 |
| WO | WO 2001/035861 | 5/2001 |
| WO | WO 2001/35870 | 5/2001 |
| WO | WO 2001/072239 | 10/2001 |
| WO | WO 2002/036048 | 5/2002 |
| WO | WO 2003/011195 | 2/2003 |
| WO | WO 2003/092554 | 11/2003 |
| WO | WO 2003/028522 | 1/2004 |
| WO | WO 2004/014257 | 2/2004 |
| WO | WO 2004/014474 | 2/2004 |
| WO | WO 2004/058097 | 7/2004 |
| WO | WO 2005/011534 | 2/2005 |
| WO | WO 2005/041810 | 5/2005 |
| WO | WO 2005/087140 | 9/2005 |
| WO | WO 2006/070372 | 7/2006 |
| WO | WO 2006/085304 | 8/2006 |
| WO | WO 2006/089236 | 8/2006 |
| WO | WO 2006/127765 | 11/2006 |
| WO | WO 2007/025028 | 3/2007 |
| WO | WO 2007/034488 | 3/2007 |
| WO | WO 2007/058857 | 5/2007 |
| WO | WO 2007/123658 | 11/2007 |
| WO | WO 2007/134290 | 11/2007 |
| WO | WO 2008/005535 | 1/2008 |
| WO | WO 2008/013915 | 1/2008 |
| WO | WO 2008/070797 | 6/2008 |
| WO | WO 2008/091515 | 7/2008 |
| WO | WO 2008/103722 | 8/2008 |
| WO | WO 2008/150529 | 12/2008 |
| WO | WO 2009/026563 | 2/2009 |
| WO | WO 2009/033469 | 3/2009 |
| WO | WO 2009/045331 | 4/2009 |
| WO | WO 2009/052188 | 4/2009 |
| WO | WO 2009/053497 | 4/2009 |
| WO | WO 2009/091509 | 7/2009 |
| WO | WO 2009/094500 | 7/2009 |
| WO | WO 2009/134701 | 11/2009 |
| WO | WO 2009/137359 | 11/2009 |
| WO | WO 2009/149462 | 12/2009 |
| WO | WO 2009/155561 | 12/2009 |
| WO | WO 2010/008549 | 1/2010 |
| WO | WO 2010/037141 | 4/2010 |
| WO | WO 2010/040009 | 4/2010 |
| WO | WO 2010/057262 | 5/2010 |
| WO | WO 2010/098857 | 9/2010 |
| WO | WO 2010/138853 | 12/2010 |
| WO | WO 2011/025945 | 3/2011 |
| WO | WO 2011/081997 | 7/2011 |
| WO | WO 2011/109801 | 9/2011 |
| WO | WO 2011/137531 | 11/2011 |
| WO | WO 2011/109813 | 1/2012 |
| WO | WO 2012/035279 | 3/2012 |
| WO | WO 2012/095455 | 7/2012 |
| WO | WO 2012/162228 | 11/2012 |
| WO | WO 2012/177942 | 12/2012 |
| WO | WO 2013/028387 | 2/2013 |
| WO | WO 2013/012801 | 4/2013 |
| WO | WO 2013/059747 | 4/2013 |
| WO | WO 2013/086413 | 6/2013 |

OTHER PUBLICATIONS

U.S. Appl. No. 29/484,001, filed Mar. 5, 2014, Pesce et al.
U.S. Appl. No. 14/197,590, filed Mar. 5, 2014, Ratz et al.
U.S. Appl. No. 14/197,639, filed Mar. 5, 2014, Ratz et al.
U.S. Appl. No. 14/197,690, filed Mar. 5, 2014, Ratz et al.
"Company Overview," Jun. 25, 2009 at TVT.
"Update," believed to be presented on Jun. 6, 2010 Applicant believes this may have been presented on Jun. 6, 2010 at TVT.
Bavaria, Joseph E. M.D. et al.: "Transcatheter Mitral Valve Implantation: The Future Gold Standard for MR?," Applicant requests the Examiner to consider this reference to be prior art as of Dec. of 2010.
Bavaria, Joseph E. M.D.: "CardiAQ Valve Technologies: Transcatheter Mitral Valve Implantation," Sep. 21, 2009.
Berreklouw, Eric, Md, PhD, et al., "Sutureless Mitral Valve Replacement With Bioprostheses and Nitinol Attachment Rings: Feasibility in Acute Pig Experiments," the Journal of Thoracic and Cardiovascular Surgery, vol. 142, No. 2, Aug. 2011 in 7 pages, Applicant believes this may have been available online as early as Feb. 4, 2011.

(56) References Cited

OTHER PUBLICATIONS

Boudjemline, Younes, Md, et al., "Steps Toward the Percutaneous Replacement of Atrioventricular Valves," JACC, vol. 46, No. 2, Jul. 19, 2005:360-5.

Brinkman, William T., MD, et al., Transcatheter Cardiac Valve Interventions, Surg Clin N Am 89 (2009) 951-966, Applicant believes this may have been available as early as Aug. of 2009.

Businesswire.com, "CardiAQ Valve Technologies (CVT) Discloses Successful Results of Acute in Vivo Study of its Novel Transcatheter Mitral Valve Implantation (TMVI) System," Sep. 28, 2009.

Businesswire.com, CardiAQ Valve Technologies, "CardiAQ Valve Technologies ("CVT") to disclose data during 'EuroPCR 2010' about the world's first successful in vivo transcatheter delivery of a mitral heart valve implant," Irvine, California, May 20, 2010.

CardiAQ Valve Technologies Company Fact Sheet 2009.

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. of 2006.

European Extended Search Report for EP App. No. EP 06 827 638, dated Feb. 28, 2013.

Feldman, Ted, MD. "Prospects for Percutaneous Valve Therapies," Circulation 2007;116:2866-2877. Applicant believes that this may be available as early as Dec. 11, 2007.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Grube, Eberhard, MD, et al., "Percutaneous Implantation of the CoreValve Self-Expanding Valve Prosthesis in High-Risk Patients With Aortic Valve Disease, The Siegburg First-in-Man Study" Journal of the American Heart Association, 2006; 114:1616-1624, originally published online Oct. 2, 2006.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.

International Search Report and Written Opinion for PCT/US2006/043526, dated Jun. 25, 2008.

International Search Report and Written Opinion for PCT/US2009/058893, dated Dec. 11, 2009.

International Search Report and Written Opinion for PCT/US2010/031313, dated Dec. 22, 2010.

International Search Report and Written Opinion for PCT/US2011/041306, dated Feb. 29, 2012.

International Search Report and Written Opinion for PCT/US2011/053138, dated Apr. 24, 2012.

JenaValve Technology, "The JenaValve—The Prosthesis", 2011 JenaValve Technology in 1 page.

Karimi, Houshang, MD, et al., "Percutaneous Valve Therapies," SIS 2007 Yearbook, Chapter 11, pp. 1-11.

Kronemyer, Bob: "CardiAQ Valve Technologies: Percutaneous Mitral Valve Replacement," Start Up—Windhover Review of Emerging Medical Ventures, vol. 14, Issue No. 6, Jun. 2009, pp. 48-49.

Lauten, Alexander, et al., "Experimental Evaluation of the JenaClip Transcatheter Aortic Valve," Catheterization and Cardiovascular Interventions 74:514-519, published online May 11, 2009, Applicant believes this may have been available online as early as Apr. 27, 2009.

Leon, Martin B., Md, et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lozonschi, Lucian, Md, et al., "Transapical Mitral Valved Stent Implantation," Ann Thorac Surg 2008;86:745-8 in 4 pages, Applicant believes this may have been available as early as Sep. of 2008.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "'Double-Crowned Valved Stents for Off-Pump Mitral Valve Replacement," European Journal of Cardio-thoracic Surgery 28 (2005) 194-199, Applicant believes this may have been available as early as Aug. of 2005.

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

Mack, Michael, M.D., "Antegrade Transcatheter Mitral valve Implantation: A Short-term Experience in Swine Model," Applicant believes this may have been presented on May of 2011 at TVT.

Mack, Michael, M.D., "Antegrade Transcatheter Mitral valve Implantation: On-Going Experience in Swine Model," Applicant believes this may have been presented on Nov. of 2011 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

Neovasc corporate presentation, Oct. 2009, available at http://www.neovasc.com/investors/documents/Neovasc-Corporate-Presentation-October-2009.pdf.

Ostrovsky, Gene, "A Trial of Zenith Fenestrated AAA Endovascular Graft Goes On," medGadget, Aug. 1, 2008, available at: :http://www.medgadget.com/2008/08/a_trial_of_zenith_fenestrated_aaa_endovascular_graft_goes_on.html.

Ostrovsky, Gene: "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Piazza, Nicoló, MD, et al., "Anatomy of the Aortic Valvar Complex and its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. of 2008.

Pluth, James R., M.D., et al., "Aortic and Mitral Valve Replacement with Cloth-Covered Braunwald-Cutter Prosthesis, A Three-Year Follow-up," the Annals of Thoracic Surgery, vol. 20, No. 3, Sep. 1975, pp. 239-248.

Quadri, Arshad M.D., "Transcatheter Mitral Valve Implantation (TMVI) (An Acute In Vivo Study)," Applicant believes this may have been presented on Sep. 22, 2010 at TCT.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Ratz, J. Brent et al., "Fabric, Skin, Cloth expansion . . . best approach?," AREA by Autodesk, 3ds Max: Modeling, Forum postings from Feb. 18, 2009 to Feb. 19, 2009, http://area.autodesk.com.

Ratz, J. Brent et al., "Isolating Interpolation," Arch-Pub.com, Architecture Forums: Animation and Rigging, Forum postings from Feb. 9, 2009 to Feb. 10, 2009, http://www.arch-pub.com.

Ratz, J. Brent, "In3 Company Overview," Jun. 24, 2009.

Ratz, J. Brent, "LSI EMT Spotlight," May 15, 2009.

(56) References Cited

OTHER PUBLICATIONS

Ruiz, Carlos E., "Overview of Novel Transcatheter Valve Technologies," Applicant believes this may have been presented on May 27, 2010 at EuroPCR.

Seidel, Wolfgang, et al., "A Mitral Valve Prosthesis and a Study of Thrombosis on Heart Valves in Dogs," JSR—vol. II, No. 3—May, 1962, submitted for publication Oct. 9, 1961.

Spillner, J. et al., "New Sutureless 'Atrial-Mitral-Valve Prosthesis' for Minimally Invasive Mitral Valve Therapy," Textile Research Journal, 2010, in 7 pages, Applicant believes this may have been available as early as Aug. 9, 2010.

Van Mieghem, et al., "Anatomy of the Mitral Valvular Complex and its Implications for Transcatheter Interventions for Mitral Regurgitation," J. Am. Coll. Cardiol., 56:617-626 (Aug. 17, 2010).

Vu, Duc-Thang, Md, et al., "Novel Sutureless Mitral Valve Implantation Method Involving a Bayonet Insertion and Release Mechanism: a Proof of Concept Study in Pigs," the Journal of Thoracic and Cardiovascular Surgery, vol. 143, No. 4, 985-988, Apr. 2012, Applicant believes this may have been available online as early as Feb. 11, 2012.

Walther, Thomas et al., "Transapical Approach for Sutureless Stent-Fixed Aortic Valve Implantation: Experimental Results," European Journal of Cardio-thoracic Surgery 29 (2006) 703-708, Applicant believes this may have been available as early as May of 2006.

Wayback Machine, Neovasc Ostial Products Overview, https://web.archive.org/web/20090930050359/https://www.neovasc.com/vascular-products/ostialproducts/default.php, indicated as archived on Sep. 30, 2008.

Webb, John G., et al., Transcatheter Aortic Valve Implantation: The Evolution of Prostheses, Delivery Systems and Approaches, Archives of Cardiovascular Disease (2012) 105, 153-159, Applicant believes this may have been available as early as Mar. 16, 2012.

Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.

Treede et al.: "Transapical transcatheter aortic valve implantation using the JenaValve$^{SM}$ system: acute and 30-day results of the multicentre CE-mark study." http://ejcts.oxfordjournals.org/content/41/6/e131.long. Apr. 16, 2012.

* cited by examiner

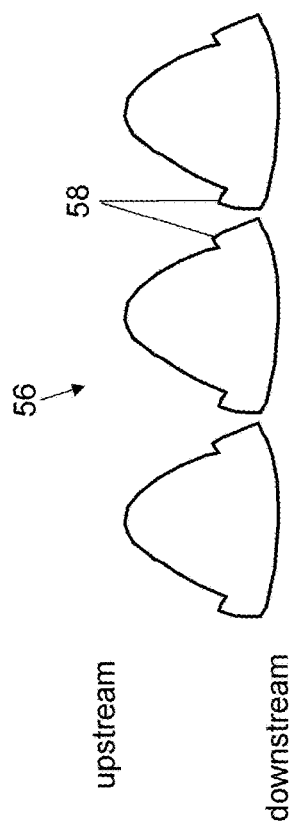
FIG. 6A
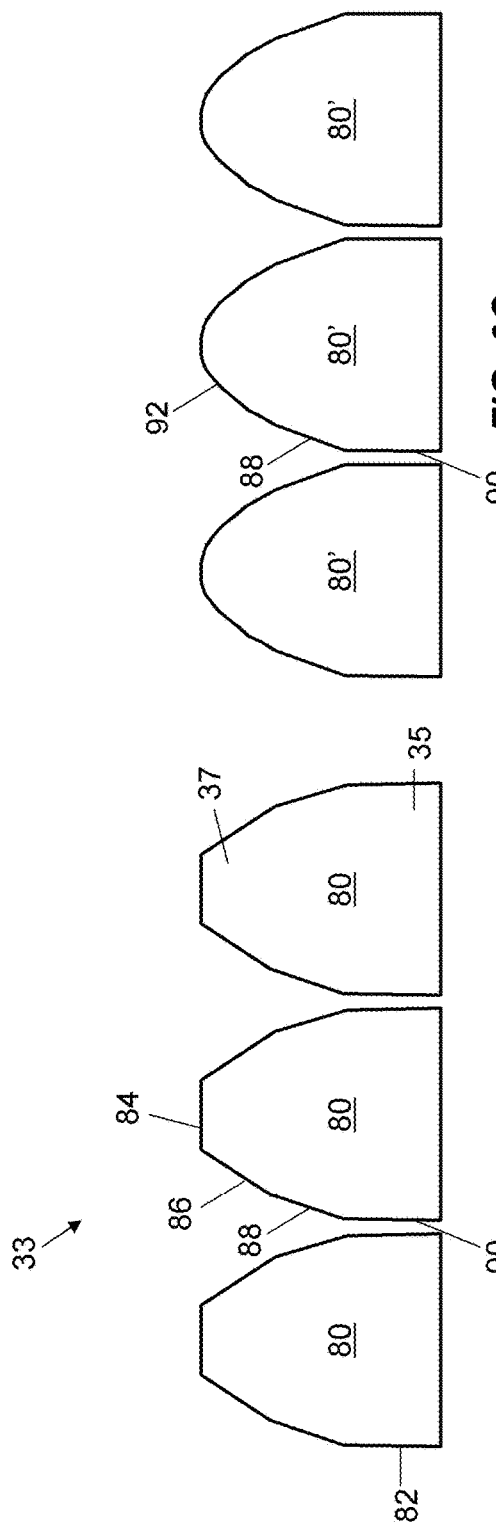
FIG. 6B
FIG. 6C

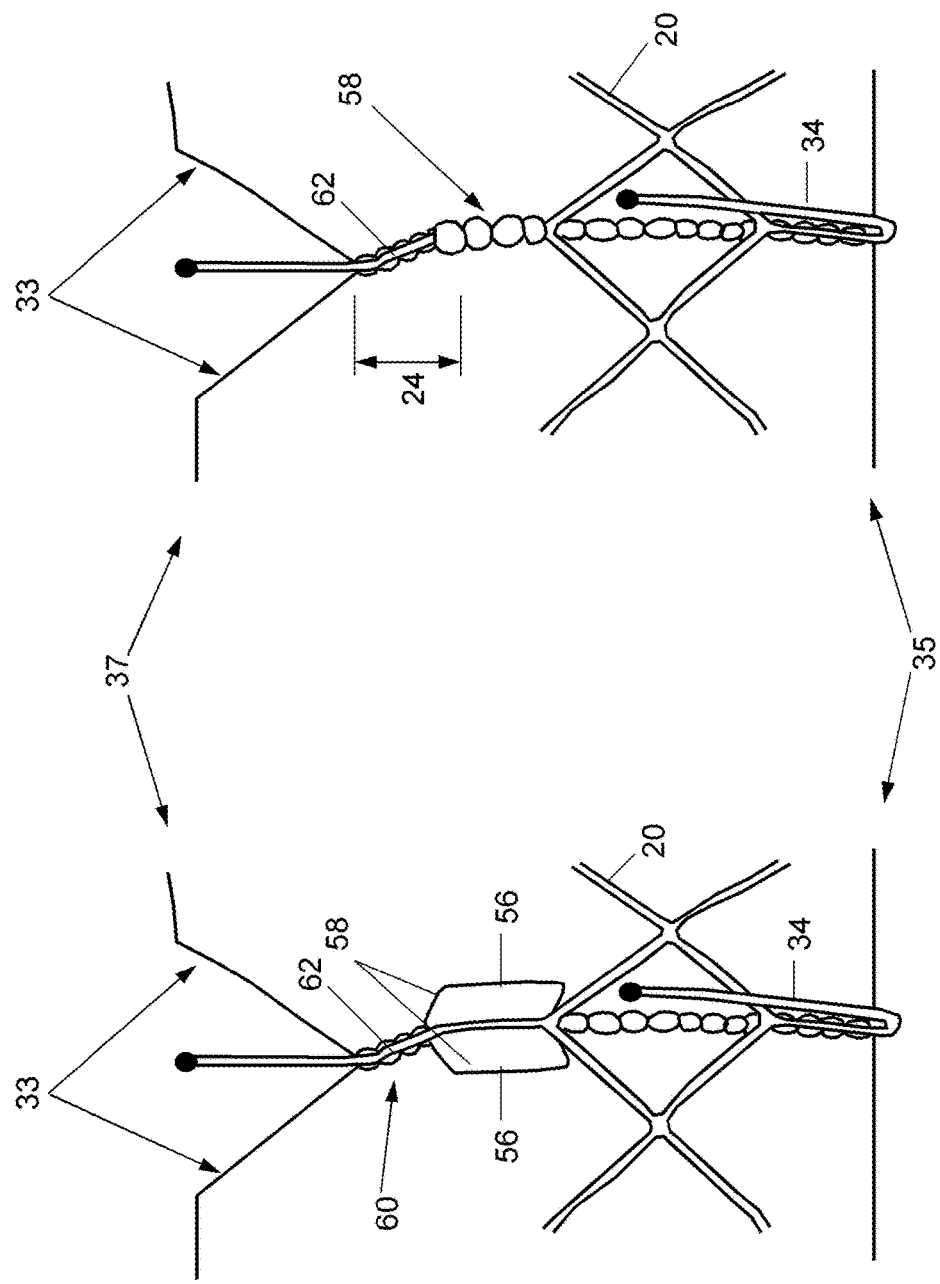

REPLACEMENT HEART VALVE AND METHOD

CROSS-REFERENCE TO RELATED APPLICATIONS

This application is a continuation of U.S. application Ser. No. 13/755,406, filed Jan. 31, 2013, which is a continuation of U.S. application Ser. No. 13/403,929, filed Feb. 23, 2012, now U.S. Pat. No. 9,730,790, which claims priority to U.S. Provisional Appl. No. 61/445,963, filed Feb. 23, 2011. This application is also related to U.S. application Ser. No. 12/569,856, filed Sep. 29, 2009, Ser. No. 12/761,349, filed Apr. 15, 2010, Ser. No. 13/165,721, filed Jun. 21, 2011, and Ser. No. 13/244,080, filed Sep. 23, 2011. These related applications provide context for the present disclosure, and in some instances the present disclosure describes embodiments and principles that build on the previous applications. All of the above applications are hereby incorporated herein by reference in their entirety and are to be considered a part of this specification.

BACKGROUND

Field of the Invention

Certain embodiments disclosed herein relate generally to replacement valves for a vascular system. In particular, the valves relate to replacement heart valves, such as for the mitral valve.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatus to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of replacement heart valves that can be compacted for delivery and then controllably expanded for controlled placement, and the related delivery devices have proven to be particularly challenging.

SUMMARY

Accordingly, there is in the need of the art for improved replacement heart valves, among other things.

In some embodiments a replacement heart valve can comprise an expandable frame, and a valve body. The expandable frame can be configured to engage a native valve annulus, wherein the frame extends longitudinally between an upstream end and a downstream end, the frame having a foreshortening portion at or adjacent the downstream end, the foreshortening portion comprising foreshortening cells that are longitudinally expanded when the frame is in a radially compacted state and longitudinally contracted when the frame is in a radially expanded state. The valve body can be coupled to the frame, the valve body coupled to the frame in the foreshortening portion in a manner so that the frame foreshortening portion can move longitudinally relative to the valve body. Upon radial compaction of the implant, the frame foreshortening portion can longitudinally expand but moves relative to the valve body so that the valve body substantially retains its longitudinal length.

According to some embodiments, a method of implanting a replacement heart valve can comprise one or more of the following steps. Advancing a replacement heart valve to a native valve annulus. Expanding a frame of the replacement heart valve from a compacted position to a first expanded configuration such that anchors on the replacement heart valve engage the native valve annulus. Reducing the diameter of the frame from the first expanded configuration to a second expanded configuration while the anchors remain engaged with the native valve annulus.

Reducing the diameter may further comprise deploying an outer ring positioned around the frame, the outer ring having a relaxed diameter less than a diameter of the frame when in the first expanded configuration. Reducing the diameter may further comprise tensioning a cord member disposed about the frame.

In some embodiments, a replacement heart valve can include a self-expandable frame, a valve body mounted to the self-expandable frame, and a tether or ring. The self-expandable frame can be configured to engage a native valve annulus when in an expanded configuration. The self-expandable frame can have a first diameter when in a relaxed, fully expanded configuration. The valve body can include a plurality of valve leaflets configured to open to allow flow in a first direction and engage one another so as to close and prevent flow in a second direction, the second direction being opposite the first direction. The tether or ring can have a second diameter when in a relaxed, fully expanded configuration, the tether or ring being fit about a portion of the self-expandable frame, where the first diameter is greater than the second diameter.

In some embodiments, a replacement heart valve can comprise an expandable frame configured to engage a native valve annulus, and a valve body mounted onto the expandable frame. The valve body can include a valve skirt configured to engage the expandable frame through a series of stitches, and a plurality of valve leaflets attached to the valve skirt. An upstream edge of each valve leaflet can be arcuate and a portion of the skirt can have an arcuate upstream edge substantially aligned with the valve leaflet upstream edges, wherein the aligned skirt and valve leaflet upstream edges can be attached to one another.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIG. 4A is a schematic side view of the anchors of the replacement heart valve implant of FIG. 1.

FIGS. 4B-E are schematic side views of reverse foreshortening anchors of another embodiment of replacement heart valve.

FIG. 6A is a side view of portions of an embodiment of valve leaflets of a replacement heart valve.

FIGS. 6B-6C are portions of embodiments of valve skirts for replacement heart valves.

FIGS. 7A-7B are side views of a portion of the replacement heart valve of FIG. 1 in various stages of assembly in the expanded state.

DETAILED DESCRIPTION

The associated drawings and specification discuss aspects and features of the present invention in the context of several different embodiments of heart valve implants, delivery devices and methods that are configured for use in the vasculature of a patient. Discussing these features in connection with heart valve implants employing stents provides for clarity and consistency in presenting these inventive features and concepts. However, it is to be understood that the features and concepts discussed herein can be applied to products other than heart valve implants.

Figure 1:
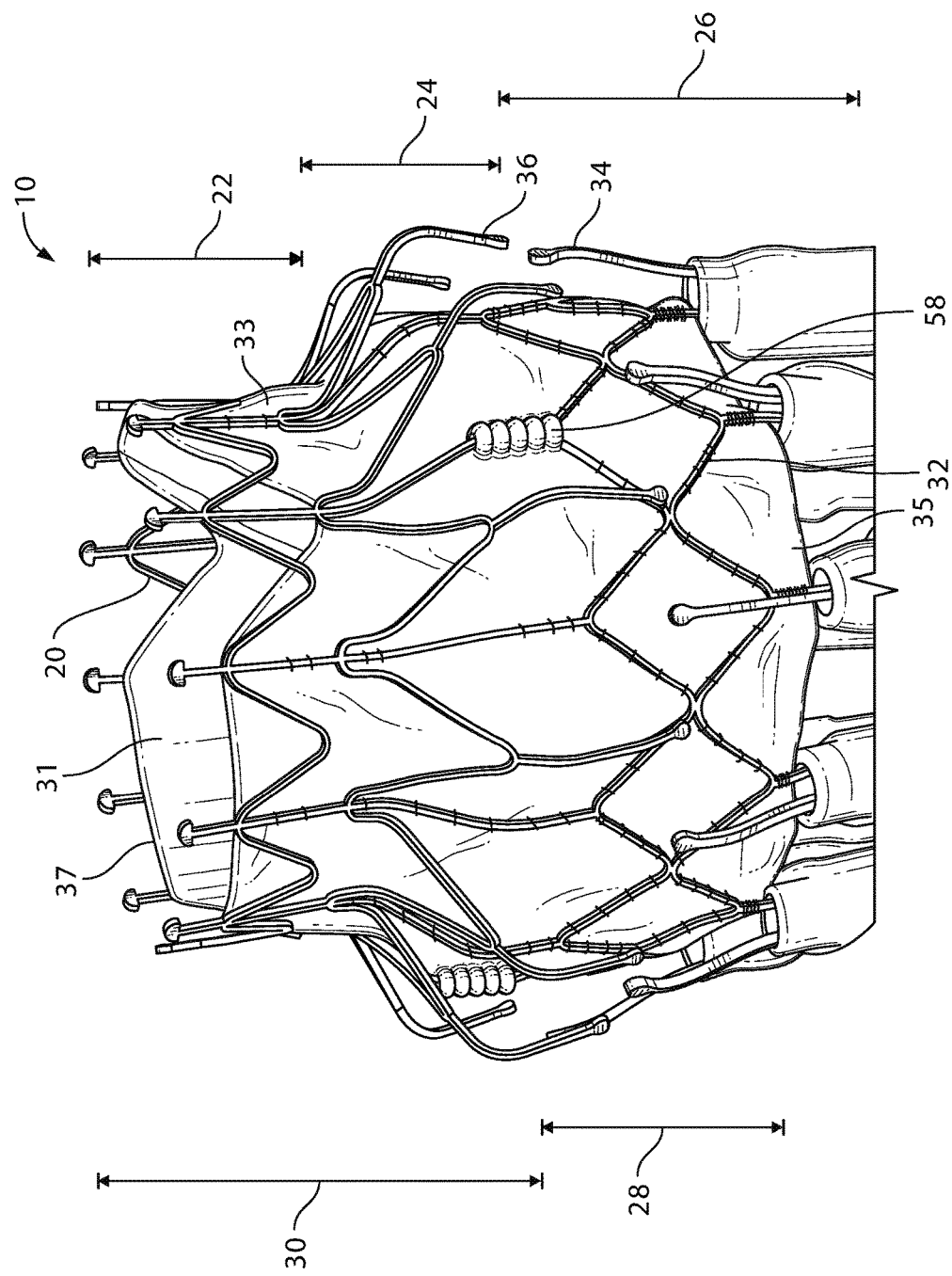
FIG. 1 illustrates a side view of a replacement heart valve implant in an expanded state in accordance with one embodiment.

FIG. 1 illustrates one embodiment of a replacement heart valve 10. The illustrated replacement heart valve 10 is designed to replace a diseased native mitral valve. One of any number of different heart valve designs could be used. In this embodiment, the replacement heart valve 10 is made up of an expandable frame 20 to which a valve body 31 is attached. The expandable frame 20 can be configured to engage a native valve annulus with anchors 34, 36. The valve body 31 can include flexible leaflets that open and close, as discussed in the related applications previously incorporated by reference. Thus, the implanted replacement heart valve 10 can be secured to the native valve annulus with the frame 20 and the valve body 31 can regulate the flow of blood through the valve.

As shown in FIG. 1, the valve 10 has an upstream or inflow end 22 and a downstream or outflow end 26. The frame 20 has a first diameter at the upstream end 22 that is substantially less than a second diameter at the downstream end 26. A transition portion 24 is positioned between the two ends of the frame 20.

The frame 20 can be constructed with a foreshortening portion 28 so that part of the frame foreshortens as the frame is radially expanded from a collapsed or compacted configuration. In the illustrated embodiment, the foreshortening portion 28 generally corresponds with the downstream end 26. A non-foreshortening portion 30 can extend upstream from the foreshortening portion 28, and can generally correspond with the upstream 22 and transition 24 portions. The foreshortening portion 28 can include a plurality of undulating struts that form a portion of the generally oval, diamond, or other shaped cells 32 that can extend circumferentially around the frame to form the ring, or rings, of the foreshortening portion. The cells' longitudinal length increases when the frame radially compacts and the length shortens when the frame radially expands, providing the foreshortening feature of the valve frame. The foreshortening portion 28 can include foreshortening cells 32 that are longitudinally expanded when the frame 20 is in a radially compacted state and longitudinally contracted when the frame is in a radially expanded state.

The anchors 34, 36 can be positioned to be on either side of the foreshortening portion 28. This can allow the anchors to move relative to one another. In this way, with the anchors 34, 36 positioned on either side of the valve annulus of the diseased heart valve, expansion of the frame causes the opposing anchors 34, 36 to move toward one another, and can allow the replacement heart valve to be secured to the valve annulus through the anchors grasping opposite sides of the annulus. The valve implant 10 is shown with the downstream end 26, or the downstream-most portion of the anchor 34, coupled to a loading device configured to form and load the valve implant 10 onto a delivery device.

In some instances, there is a potential for a patient, having received a replacement heart valve, to develop an enlarged valve annulus. This may be due to radially outward force exerted on the annulus by self-expanding of the replacement heart valve over an extended period of time, among other features. An enlarged mitral valve annulus can impair valve function and result in left atrial and ventricular enlargement and significant mitral regurgitation. Accordingly, there is a need in the art for apparatus and methods to mitigate the risk of valve frame induced enlargement of the annulus.

In some embodiments, a heart valve implant 10' can be expanded to a first installed diameter D1 (FIG. 2A) upon initial deployment and reconfigured to a second installed diameter D2 (FIG. 2B) that is less than the first installed diameter D1. The reduced size of the second installed diameter D2 can facilitate a reduced radial load on the native annulus after complete deployment of the heart valve implant 10' at the mitral valve annulus.

Figure 2A:
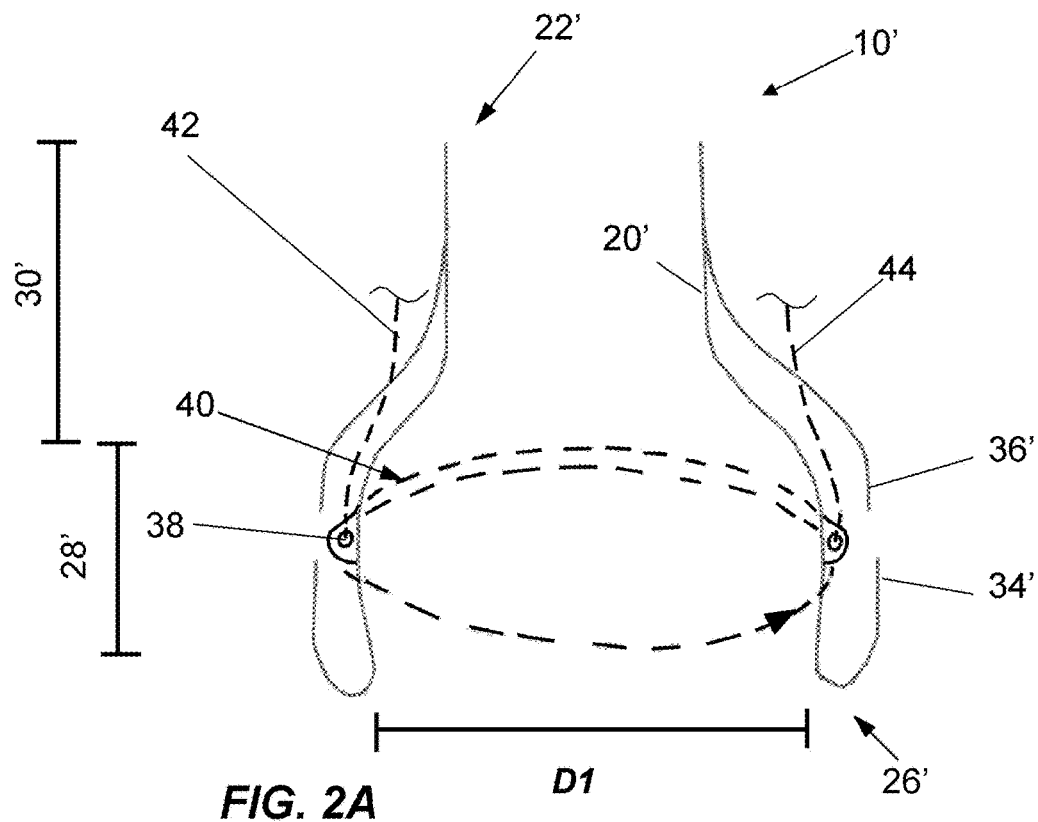
FIG. 2A is a schematic side view of another replacement heart valve implant in a first expanded state.
Figure 2B:
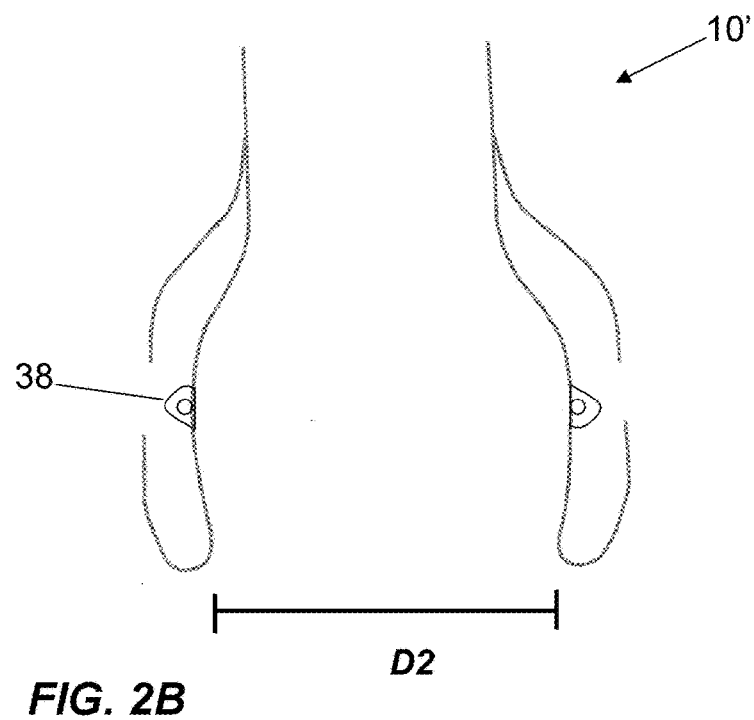
FIG. 2B is a schematic side view of the replacement heart valve of FIG. 2A in a second expanded state.

The embodiment illustrated in FIGS. 2A and 2B is a schematic view of the heart valve implant 10' in expanded states. Numerical reference to components is the same as previously described, except that a prime symbol (') has been added to the reference. Where such references occur, it is to be understood that the components are the same or substantially similar to previously-described components. It should be understood that the illustrated heart valve implant includes each of the features designated by the numbers used herein. However, as emphasized repeatedly herein, these features need not be present in all embodiments.

With continued reference to FIGS. 2A and 2B, the frame 20' can include one or more connector eyelets 38. In some embodiments, the frame 20' can include a plurality of eyelets 38, such as eyelets on a plurality of struts and/or rings of the frame. As shown, the eyelets 38 are positioned within, or adjacent, the foreshortening portion 28' of the downstream end 26' of the frame. The eyelets 38 can be configured to receive and/or enclose a connector member 40, such as a tether, cord, fiber, or the like. In the illustrated embodiment, the plurality of eyelets 38 protrude from the frame 20' to provide relatively simple access for the tether 40 and little resistance to movement of the tether through the plurality of eyelets. As shown, the tether 40 is threaded through the eyelets 38 about the circumference of the frame 20'. The first and second ends 42, 44 of the tether 40 extend proximally past the upstream end 22'. It will be understood that the eyelets 38 and tether 40 can be positioned around any portion of the frame 20' that is expandable and compressible.

In some embodiments, only some of the eyelets 38 protrude outward from the frame 20'. More particularly, the eyelets 38 can protrude outward where the tether 40 transitions from extending circumferentially around the frame 20' to extending in a longitudinal direction, such as toward a delivery device or system. In some embodiments, the eyelets 38 can lie on the same plane as the frame struts so as not to protrude radially inward or outward from the frame. For example, the eyelet 38 can be positioned within the same diametral geometry as the frame. In some embodiments, the eyelets 38 are fully enclosed loops that can be circular (FIG. 2A), oval, or any other geometric shape. In some embodiments, the eyelets can have a discontinuous loop, or diameter, and the eyelet loop can be separable or opened between two portions of the loop. In some embodiments, the eyelet is less than a full loop, e.g. a hook, or partial loop, or the like.

The number of eyelets 38 can vary based upon the characteristics of the frame, the tether, and the intended deployment of the valve implant. For example, a larger diameter frame can include a greater number of eyelets to securely affix the tether to the frame and prevent movement, or creep, of the tether subsequent to the deployment of the valve frame.

The eyelets 38 can be formed, or fabricated, as an integral part of the frame 20' and machined, cut, formed, stamped, or the like, out of the same tube material as the remaining portions of the frame. In some embodiments, the eyelets 38 can be separately fabricated and coupled to the frame 20' by various manufacturing methods, e.g. laser welding, brazing, adhesives, or the like.

With continued reference to FIGS. 2A and 2B, the tether 40 can be any biocompatible, flexible, suitable strength member. In some embodiments, the tether 40 can be bioabsorbable. The tether 40 can include a first end 42 and a second end 44. The first and second ends can extend proximally out of the patients' vasculature to a valve implant deployment device or other system that controls operation of the tether 40. The tether 40 can include suitable dimensions sized to be received by the eyelets. The tether length can be suitably long to have the first and second ends disposed or wrapped around the implant frame and then one or both extend longitudinally from the frame through the vasculature to the delivery device or other control system.

Preferably, the tether 40 and eyelets 38 are arranged so that the tether extends about the outer diameter of the frame 20'. In some embodiments, the tether can wrap around the frame for the full circumference, or more than a full circumference, e.g. 1¼, 1½, or the like, such that tension applied to the first and second ends of the tether reduces or limits the circumference of the frame. In some embodiments, the tether can wrap around a portion of the circumference, e.g. ½, ⅔, ¾, or the like.

A method of using the tether 40 will now be described. The tether 40 can be coupled to the compacted valve implant 10' prior to insertion and deployment of the same within the patient. The tether 40 can be wrapped around the frame 20', such as passing through eyelets 38 disposed about the foreshortening portion 28' or other portions of the frame 20'. The first 42 and second 44 ends of the tether 40 can extend proximally from a pair of longitudinal transition eyelets that preferably are generally diametrically opposed from one another on the frame. In some embodiments, the two longitudinal transition eyelets can be disposed at positions that are other than generally 180 degrees apart from one another.

The valve implant 10' can then be suitably positioned at the mitral valve annulus and radially expanded so that the anchors 34', 36' grasp the annulus on both the upstream and downstream sides of the annulus. The frame can be self-expanding, e.g. fabricated with shape memory material, or can be balloon expanded. The frame 20' can expand to a first diameter to ensure suitable engagement, or grasping, of the anchors onto, or with, the mitral valve annulus (FIG. 2A). In some embodiments, including that shown, the expanded diameter size can influence the engagement of the anchors 34', 36' because the greater the diameter, the closer the upstream and downstream anchor tips will approach one another. This is due to the foreshortening nature of the frame as previously discussed.

Once the valve implant 10' has been expanded to the first diameter D1, the tether 40 can be tensioned by pulling, or retracting, the first end 42 and/or the second end 44 of the tether 40, such as in the proximal direction. The tensioned tether can secure the frame to prevent further expansion and/or reduce the diameter of the frame. The tension can be sufficient to create an inward radial force on the frame to overcome radial outward self-expansion force of the frame. The greater inward radial force can reduce the diameter of the frame. The first end 42 and the second end 44 can be pulled in tension until the diameter of the frame achieves a suitable reduced second diameter D2. The tensioned tether 40 can reduce the radial force exerted on the valve annulus and reduce the risk of an enlarged mitral valve annulus over an extended period of time. Also, the diameter can preferable be dialed in to the desired effective size for the valve implant 10'.

In some embodiments, the tether 40 can be secured in the tensioned position to maintain the frame 20' in the reduced diameter position. The tether 40 can also be secured around the foreshortening portion of a self-expanding shape memory frame. Such securement can be by any method and/or apparatus, such as knot-tying, melting, or crimping a securement structure about the tether and/or an eyelet, and the like. In some embodiments, the tether can be bioabsorbable, as described above. The tether may also be used in conjunction with a balloon expanded frame. A bioabsorbable tether can reduce the frame diameter to achieve elastic deformation and can be temporarily secured to hold the frame diameter until the tether is absorbed into the body. In some embodiments, the tether is not required to be secured and can be removed from the body after the frame diameter is reduced.

In another embodiment, the second end 44 of the tether 40 is tied or otherwise bonded to the valve frame 20'. Tether adjustment can be made by pulling on the first end 42 of the tether 40.

In another embodiment, the tether 40 may include a plurality of one-way stop members that allow a clinician to pull and tighten the tether but prevent the tether from loosening once tightened. The one-way stop members can comprise a ratcheting mechanism. The one-way stop members can each have a sloping forward surface and a perpendicular back stop surface. In other words, the one-way stop members can have a tapered surface that flares out to a back wall. As the clinician pulls on the tether, the sloped or tapered surface of a member can be pulled through the corresponding eyelet. Once the stop member is pulled through the eyelet, the back wall or stop surface can abut the eyelet. If the clinician were to release tension on the tether, the stop surface would not be able to pass back through the eyelet, and the tether thus would not loosen. As such, a clinician can reduce the diameter/circumference of a self-expanding or other type of valve frame after deployment by pulling the tether sufficient to obtain a desired maximum circumference. The one-way stop members will then prevent loosening of the tether, and thus the tether will constrain the valve frame to that maximum desired circumference. The remaining portion of the tether can then be cut and removed.

The one-way stop members can have a cross-sectional shape that is triangular, wedge shaped, bullet shaped, a half circle, arrow shaped, etc.

In still another embodiment, a ball-shaped stop is disposed at each of the tether first 42 and second 44 ends. The distance along the tether between the first and second end stops is selected as the maximum desired valve frame circumference. The tether 40 preferably is threaded through the eyelets 38 as discussed above. However the stops are sized and shaped so that they cannot be pulled through the eyelets. When the valve frame is compacted prior to deployment, the tether fits relatively loose around the frame. Upon deployment the valve frame is allowed to expand until the stops engage corresponding eyelets, defining a maximum expansion size. Of course it is to be understood that the tether stops could be constructed in various shapes and sizes other than the ball-shaped stops described.

In some embodiments, a self-expanding valve frame is configured to have a relaxed diameter and circumference that is greater than ultimately desired. As such, the valve frame is biased to expand to that size. However as the frame expands, eventually the first and second stops will each abut corresponding eyelets and thus prevent further expansion beyond the desired diameter and circumference as defined by the tether. Since the self expanding frame is biased to expand further, it will resist other forces within the heart that would tend to compress and/or otherwise deform the valve frame.

In yet another embodiment, the tether comprises a loop that is flexible, but resists stretching. The tether preferably is threaded through the eyelets. When the valve frame is compacted prior to deployment, the tether fits relatively loose around the frame. Upon deployment the valve frame is allowed to expand until the maximum diameter of the tether loop is reached, defining a maximum expansion size.

Figure 3A:
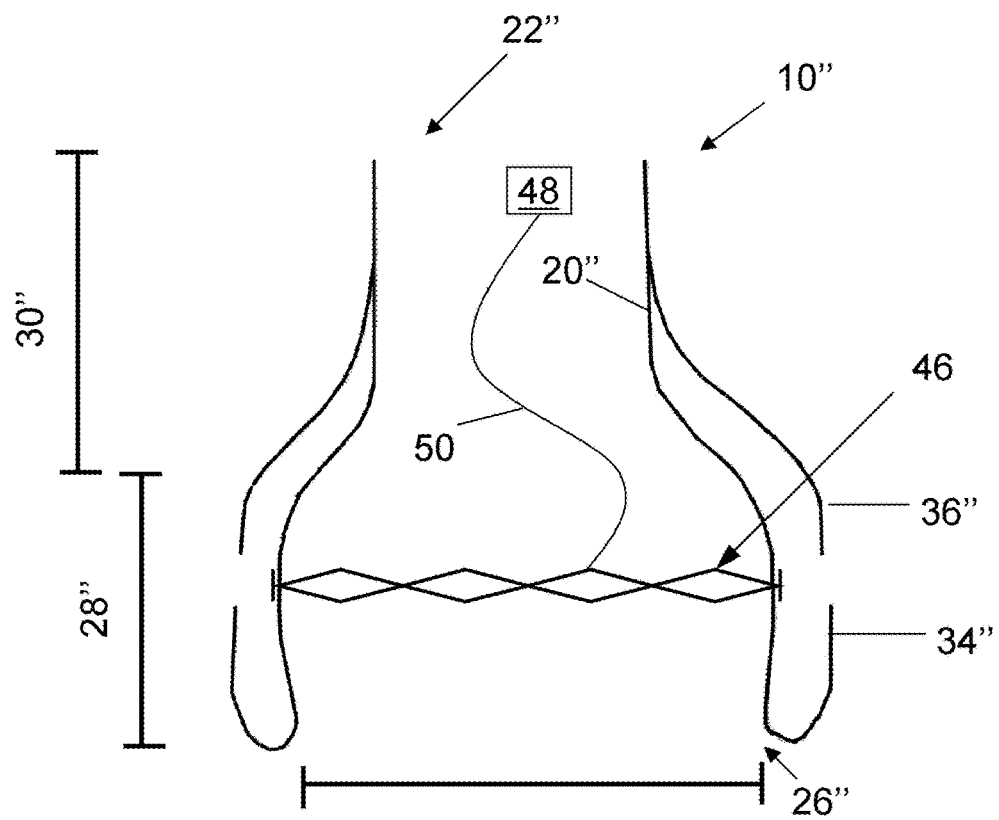
FIG. 3A is a schematic side view of another replacement heart valve implant in a first expanded state.
Figure 3B:
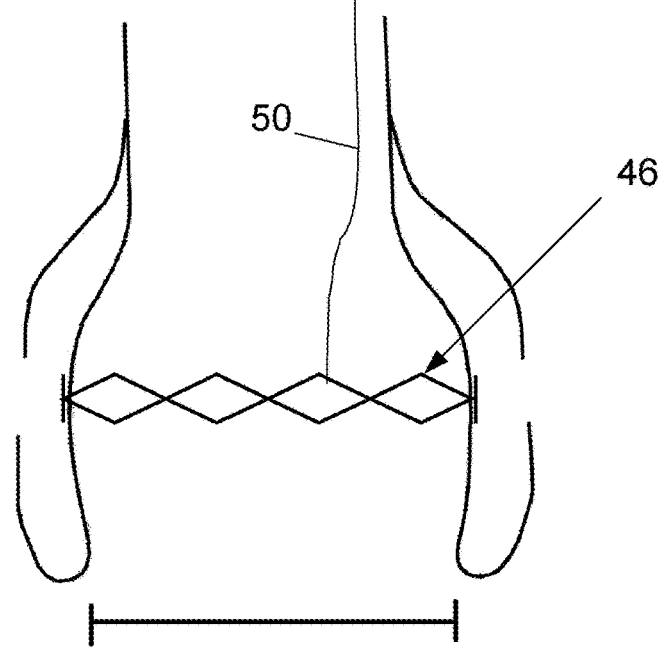
FIG. 3B is a schematic side view of the replacement heart valve of FIG. 3A in a second expanded state.

With reference now to the illustrated embodiment of FIGS. 3A and 3B, a perspective view of another embodiment of a heart valve implant 10″ in expanded states is shown. Numerical reference to components is the same as previously described, except that prime symbols (″) have been added to the reference. Where such references occur, it is to be understood that the components are the same or substantially similar to previously-described components. It should be understood that the illustrated heart valve implant includes each of the features designated by the numbers used herein. However, as emphasized repeatedly herein, these features need not be present in all embodiments.

The heart valve implant 10″ can be similar to the embodiments described above. The frame 20″ can comprise a self-expanding material, e.g. a shape memory material, Nitinol, or the like, or can be balloon-expandable. Preferably, an outer ring 46 is disposed about the frame 20″, such as about the foreshortening portion 28″ of the frame. In the illustrated embodiment, the outer ring 46 is formed separately from the valve frame 20″. The outer ring 46 can be configured to reduce the over-expanded, or enlarged, first diameter D1 of the frame (FIG. 3A) to the desired reduced second diameter D2 (FIG. 3B), previously mentioned.

The outer ring 46 can take many forms. For example, the outer ring can form a pattern of undulating struts, a sinusoidal, or wave configuration. As illustrated, the outer ring 46 can have two rows of undulating struts to form a series of cells of various shapes. Thus, the outer ring can be a foreshortening ring or cell, comprising a row of connected ovals, diamonds, circles, or similar geometric shapes. The shapes can be coupled adjacent one another, similar to the rows establishing the foreshortening portion of the frame, described above. In some embodiments, the outer ring can comprise more than one row of similar geometric shapes. The ovals can comprise a plurality of struts, all positioned at non-zero angles relative to the longitudinal axis, with no longitudinal struts. In some embodiments, the outer ring can be a non-foreshortening ring and can comprise longitudinal struts.

The outer ring 46 can be a self-expanding ring configured to expand or compact the frame to the second diameter D2. In some embodiments, the outer ring 46 can be a shape memory material. In some embodiments, a shape memory outer ring 46 can expand or contract to the second diameter upon reaching body temperature, or some other set temperature. The outer ring can be manufactured in a similar manner as the implant frame.

The outer ring 46 can have a relaxed expanded inner diameter that is the same as or larger than the relaxed expanded outer diameter of the implant frame 20″. In some embodiments, the outer ring's relaxed expanded inner diameter can be less than the frame's relaxed expanded outer diameter, and in some such embodiments the outer ring can form an interference fit with the frame. In further embodiments, the outer ring 46 can be physically coupled to the frame 20″ by any conventional manufacturing method, e.g. laser welding, brazing, adhesives, fasteners, cables, or the like. The outer ring 46 can be coupled to the frame at one or more locations about the frame, such as coupling locations generally equally spaced about the frame. The couplings can be sufficient to prevent longitudinal migration of the outer ring about the frame. The outer ring 46 can be coupled generally in any longitudinal position along frame, including along the foreshortening portion 28″ of the valve frame 20″. In some embodiments, the outer ring can be positioned in substantially the middle longitudinal location or mid-point of the valve frame foreshortening portion.

In some embodiments, the outer ring 46 can be coupled to a power source 48, e.g. an RF power source, or the like. The power source 48 can be configured to selectively increase the temperature of a shape memory outer ring 46 to the set temperature. This can allow the device to expeditiously achieve the reduced second diameter D2, rather than to rely on the environment to heat the device to the desired set temperature.

In some embodiments, the power source 48 and the power source coupling 50 can be removable, and can be removed from the valve implant 10″ after the frame 20″ has reached the desired diameter. In some embodiments, the outer ring can have no power source coupled to the ring, and the outer ring may be configured to assume the second diameter at a slower rate than the valve frame, as the temperature of the ring approaches the heat treat set temperature at a slower rate than with the assistance of the power source.

A method of using the outer ring 46 according to an embodiment will now be described. The outer ring 46 can be coupled to or arranged over the valve frame 20″ prior to insertion of the valve implant 10″ into the body for implant deployment. The outer ring 46 can generally be compacted to a smaller diameter about the radially compacted implant 10". The outer ring 46 may be held by a retention sleeve or delivery device, or may be frozen in place. In some embodiments, the outer ring can be maintained at a temperature below normal body temperature or some other set temperature to prevent premature expansion. The outer ring can be maintained at a lower temperature by, for example, a fluid environment within the delivery catheter until a suitable time prior to the final deployment sequence.

The valve 10" can be released from the delivery device and the foreshortening portion 28" positioned adjacent the mitral valve annulus. The valve frame 20" can self-expand or be balloon expanded to the enlarged first diameter D1 and the anchors 34", 36" can engage the valve annulus on opposing sides of the annulus. The power supply 48 can then provide energy to increase the temperature of the outer ring 46. For example, RF energy can be delivered via the power source coupled to the outer ring. The increase in temperature can change the outer ring shape as the ring recovers to the heat treated set shape memory of the reduced second diameter D2. The radially inward force of the outer ring 46 is greater than the radially outward force of the frame 20" and the frame diameter correspondingly reduces to the reduced second diameter D2 and/or is prevented from further radial expansion due to the radially-inward force applied by the outer ring 46. The reduced diameter preferably does not detrimentally affect anchor engagement as the upstream to downstream anchor tip distance can be minimally increased as the frame diameter reduces to the second diameter.

It will be understood that though the frame is generally described as moving from a first diameter D1 to a second diameter D2, the frame may expand to the desired diameter without an intermediate step. The outer ring, tether, or other devices can be used to limit or control the expansion of the frame.

In another embodiment, the valve implant can have a self-expanding frame heat treated to self-expand to the second reduced diameter and yet be balloon expanded beyond the reduced second diameter to the enlarged first diameter. The frame upstream and downstream anchors can engage the mitral valve annulus to grasp the opposing sides of the annulus in the enlarged radius configuration. The balloon can be deflated after suitable anchor engagement is verified, e.g. by observation methods, or the like. The frame can then return to the heat treated reduced second diameter without the balloon outward radial force applied to the frame inner diameter. This can be done in many ways, including heating through body temperature or coupling the frame to a power source similar to that described above.

Figure 4C:
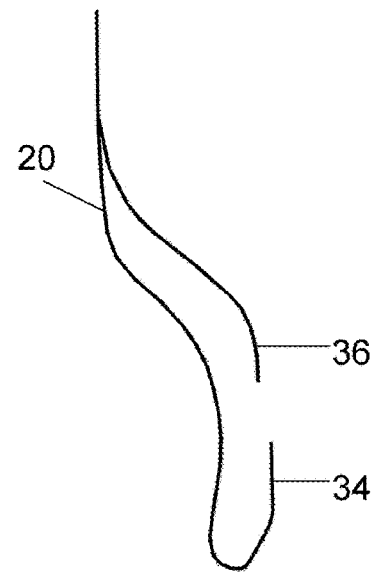

Moving now to FIGS. 4A-E, various embodiments of anchors are shown. FIG. 4A schematically illustrates the anchors 34, 36 of the heart valve implant 10 of FIG. 1. In some embodiments, the valve frame can include one or more reverse foreshortening anchors 52, 54 as shown in FIG. 4B. This may or may not be in combination with the above described foreshortening anchors 34, 36. The reverse foreshortening anchors 52, 54 can have upstream and downstream distal tips where the longitudinal spaced distance between the two sets of tips increases when the frame radially expands, and decreases when the frame radially compacts. The reverse foreshortening feature provides additional engaging, or grasping, function for the anchors to remain securely engaged with the mitral valve annulus when the frame diameter changes to a reduced second diameter.

Figure 4D:
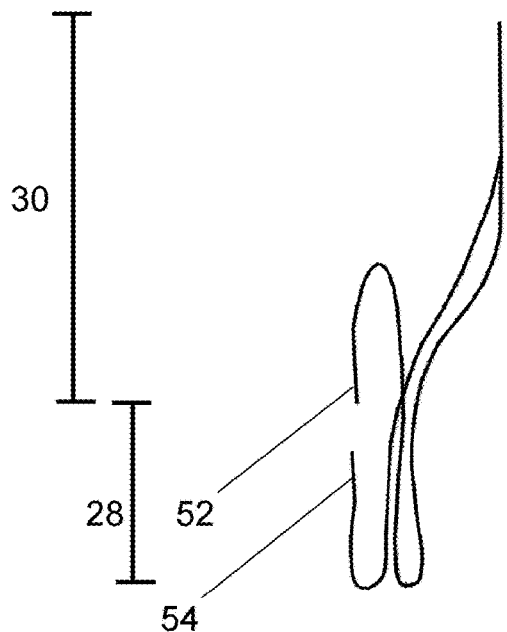
Figure 4E:
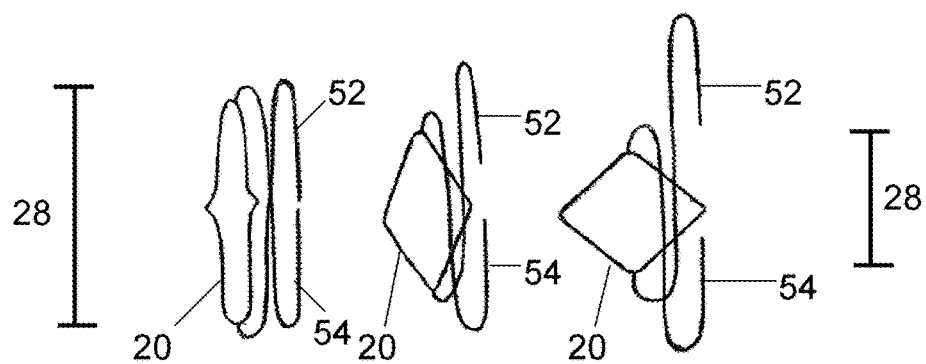

With continued reference to FIG. 4B, the reverse foreshortening anchors 52, 54 each extend from one side of the foreshortening portion 28 to the other opposing side of the foreshortening portion, but in opposite fashion. The anchor bends back on itself 180 degrees to have the anchor tip point in the opposite longitudinal direction from where the anchor first originated. In this way, the anchor tips will move towards each other when the foreshortening portion 28 is lengthened (FIG. 4C) and the tips will move away when the foreshortening portion 28 is foreshortened (FIG. 4E), as illustrated in FIGS. 4C-E. This is the opposite of the embodiments previously discussed. In some embodiments, one or more of the first and second anchors can initiate from various longitudinal positions along the frame, e.g. non-foreshortening portion, the transition portion, or the like.

A method of using the reverse foreshortening anchors 52, 54 will now be described according to one embodiment. The reverse foreshortening anchors 52, 54 are generally at their closest tip to tip relative longitudinal position when the frame is in the compacted configuration. The implant 10 is delivered into the vasculature and positioned and deployed at the mitral valve native annulus. The implant frame 20 can be expanded to the enlarged first diameter and then reduced in diameter to the reduced second diameter. In some embodiments, the reduction in diameter can cause the longitudinal distance between foreshortening anchor tips to increase. In some embodiments, the reverse foreshortening anchors can be assembled in conjunction with the normal foreshortening anchors, but their anchor tips will move closer toward one another when the frame radius decreases to the reduced second diameter. In some embodiments, the reverse foreshortening anchors can be positioned at every other circumferentially spaced expanded leg position. Thus, as the normal foreshortening anchors decrease engagement, the second foreshortening anchors can increase engagement by having the reverse foreshortening movement of the anchors reduce the tip to tip gap toward one anther.

Turning now to FIGS. 1 and 5-8, additional features of replacement heart valves will be discussed. It will be understood that selected features from these embodiments can be combined with selected features of the previously described embodiments.

As has been mentioned, the replacement heart valve 10 of FIG. 1 is made up of an expandable frame 20 to which a valve body 31 is attached. The valve body 31 can be made up of a valve skirt 33 and the plurality of leaflets that are attached to the skirt and make up the functioning portion of the valve. The valve skirt 33 can be attached to the frame 20, such as by stitches. The valve skirt 33 can be stitched, or sewn, to the frame at numerous locations; this can include undulating struts, longitudinal struts, and apices joining struts.

With continued reference to FIG. 1, the valve skirt 33 can extend to the downstream end 26, of the valve frame 20 and/or replacement heart valve 10, when the frame is in the radially expanded state. The valve body 31 advantageously prevents the leakage of blood past the native annulus and the replacement implant heart valve when the valve body extends adjacent the downstream end of the frame. The valve body 31 and/or the skirt 33 can provide suitable contact with the native mitral valve leaflets to reduce the likelihood of blood leakage between the replacement valve and the native leaflets. In some embodiments, the valve body 31 can be proximally spaced from the downstream end of the radially expanded frame. In some embodiments, the downstream end 35 of the valve body 31 can be positioned a predetermined distance from the downstream end 26 of the frame, and the valve skirt can be sufficiently downstream of, or adjacent to, the native valve annulus to prevent, or to reduce the likelihood of, bypass leakage between the replacement valve and the native annulus.

Figure 5:
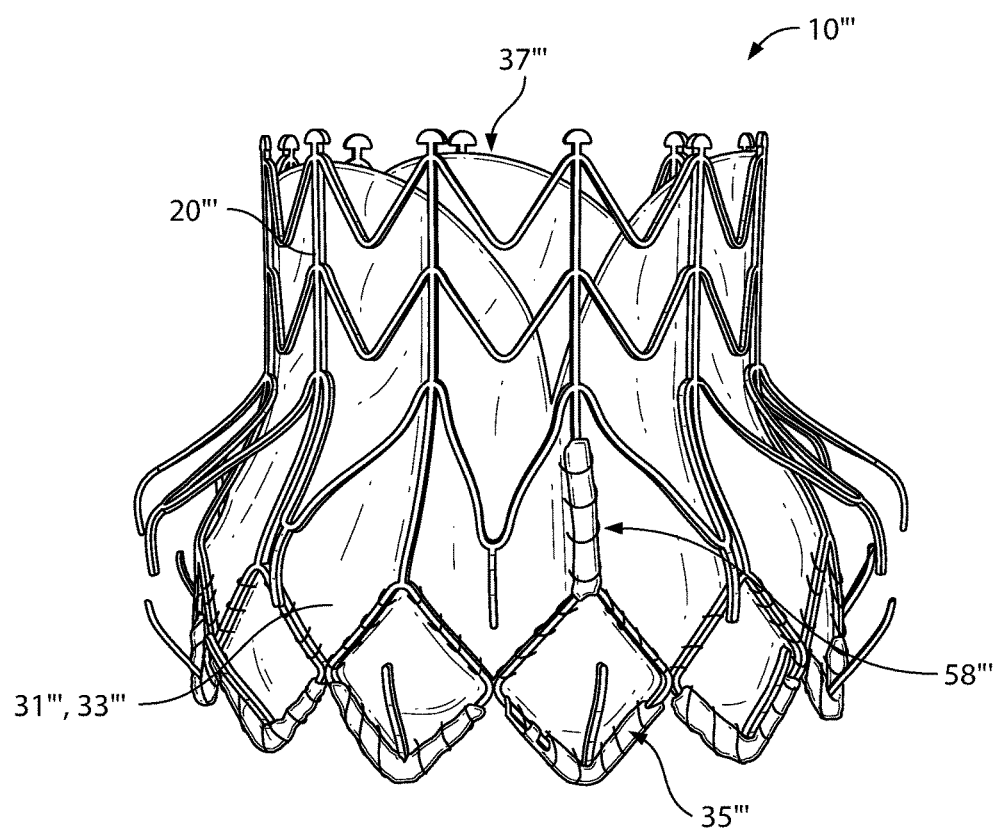
FIG. 5 is a side view of another embodiment of a replacement heart valve in an expanded state.

In some embodiments, as illustrated at FIG. 5, the downstream end 35''' of the valve skirt 33''' undulates, generally corresponding to the distal most undulating struts of the foreshortening portion on the frame 20'''. The downstream end 35''' of the valve skirt can be sized to match and be stitched to the undulating downstream struts of the frame 20'''. In this embodiment, the downstream anchors 34''' on the frame 20''' also extend in an upstream direction from the downstream apices of the foreshortening cells.

With reference to the illustrated embodiment of FIG. 5, numerical reference to components is the same as previously described, except that prime symbols (''') have been added to the reference. Where such references occur, it is to be understood that the components are the same or substantially similar to previously-described components. It should be understood that the illustrated heart valve implant includes each of the features designated by the numbers used herein. However, as emphasized repeatedly herein, these features need not be present in all embodiments.

The upstream end 37''' of the valve skirt 33''' can also vary from the upstream end 22''' of the frame 20'''. In particular, the valve skirt can have varying geometry that deviates from the upstream end. The upstream geometry 37 of the valve skirt 33 can be tapered, as shown in FIGS. 1 and 6B, or scalloped, as shown in FIGS. 5 and 6C. The furthest most upstream portion of the tapered, or scalloped arcuate, valve skirt edge can extend substantially to, or adjacent to, the upstream end of the frame.

Referring now to FIGS. 1 and 6B, the valve skirt 33 is constructed of three valve skirt pieces 80 that can be stitched together along connecting edges 82 and stitchingly fit against the frame inner portion. In the illustrated embodiment, the connecting edges 82 extend only a portion of the overall length of the skirt. The upstream end 37 of the valve skirt 33 can include an upstream substantially straight edge 84 that generally extends circumferentially along the inner surface of the frame and a tapered or angled edge 85. The substantially straight upstream edge 84 can extend substantially parallel to the upstream end 22 of the frame 20. In some embodiments, the valve skirt can include 2, 4, 5, 6 or more valve skirt pieces that can be stitched or otherwise connected together, or a single piece rolled and connected to itself. The skirt pieces can be shaped to fit together to correspond to the inner portion surface of the frame.

The different embodiments of valve skirt pieces shown in FIGS. 6B-C are generally symmetric along a longitudinal centerline of each piece. In some embodiments, the skirt pieces are not symmetric about a longitudinal centerline, for example, if different sized upstream gaps are desired between the skirt pieces. The skirt can generally include an upstream portion, a middle portion, and a downstream portion.

The valve skirt pieces 80 of FIG. 6B have an upstream portion 37 with a first tapered edge portion 84 on both longitudinal sides of the upstream end. The first tapered edge 84 can extend at an angle to approximately a location corresponding to the beginning of the transition portion of the frame. The angle of the taper can range between about 10 degrees to about 80 degrees from the upstream end. The angle can be used in part as a factor to determine the size, or area, of the blood flow passageway between the inner and outer portions of the frame upstream end.

The skirt pieces 80 can also include a second straight tapered edge portion 88, or transition edge, shaped to accommodate the change in diameter of the frame transition portion when attached to the second tapered edge 88 of an adjoining skirt piece 80. In some embodiments, the second tapered edge 88 can extend at a different angle than the first tapered edge 86. In some embodiments, the second tapered edge 88 can have the same angle as the first tapered edge 86. A downstream edge 90 of each skirt piece is shaped to accommodate the larger diameter of the expanded downstream frame portion when attached to the downstream edge 90 of an adjoining skirt piece 80. In the illustrated embodiment, the connecting edge 82 is made up of the stitched together transition edges 88 and downstream edges 90 of adjoining skirt pieces 80.

Referring primarily to FIG. 6C, but also to FIG. 5, in another embodiment, each valve skirt piece 60' can include an arcuate upstream edge 92 forming part of a scalloped portion. The upstream edge of the skirt generally can be the center, or mid-point, of one of the plurality of the valve skirt pieces. The three upstream arcuate edges 92 formed with the assembled valve skirt can span the inner diameter of the frame. Preferably each arcuate edge 92 extends to a straight transition edge 88, which in turn extends to a downstream edge 90. The transition edge 88 and downstream edge 90 are shaped so that, when stitched together, they accommodate the frame. However, the scalloped arcuate edges 92 remain unattached to one another.

In the illustrated embodiments, the stitches adjoining skirt edges is positioned generally in line with longitudinal struts of the frame, and are stitched to the frame as shown in FIGS. 1 and 5. It is to be understood that differently shaped skirt pieces may be used to accommodate differently shaped frames, such as frames without a transition portion.

In some embodiments, the angle or radius of the arcuate edge can vary, providing different sized spaced gap areas between the valve skirt pieces in the upstream portion of the frame. The spaced gap area between the valve skirt pieces advantageously provides a flow path for blood to pass between the inner surface and the outer surface of the upstream portion of the valve implant. The spaced gap establishes reduced valve body surface coverage on the frame, which reduces the frame's impact on blood flow about the implant upstream end. The upstream portion of the valve implant is generally positioned in the left atrium after complete deployment, and the flow path areas reduce any flow impact or flow restrictions in the left atrium attributable to the replacement valve implant. The spaced gap also reduces the valve body mass, or volume, in the frame upstream portion. The reduced mass, or volume, reduces the compacted storage volume required to store the replacement heart valve in a reduced diameter tube-like body.

With reference to FIG. 6A, a valve leaflet 56 embodiment is shown. Valve skirt 33 and leaflet pieces 56 can be stitched together and implemented onto the frame to form the valve body 31. The three valve leaflets shown in FIG. 6A each include two commissural tabs 58, one tab on opposing sides of the leaflet at the downstream end of each leaflet. The tabs 58 can be stitched between and to the valve skirt pieces and the valve frame such that the tabs protrude radially outwardly through the skirt longitudinal stitch as will be described in more detail below (FIGS. 1 and 5). The upstream arcuate edges of the leaflets can be stitched to the valve skirt. For example, in FIG. 5, the upstream arcuate edges of the leaflets are aligned and attached to the upstream arcuate edges 92 of the skirt so that the upstream edges of the skirt and the leaflets are substantially aligned about the circumference of the valve.

With reference to FIGS. 7A-B, a portion of a valve body assembly sequence is shown. The illustrated embodiment includes a portion of the implant coupling between the valve body 31 and the frame 20. The pieces of the valve skirt 33 can be stitched together by a longitudinal stitch 60 and the leaflet portions 56 can be wrapped around and stitched to the frame longitudinal strut 62. The longitudinal stitch 60 between two adjacent valve skirt pieces can be circumferentially positioned in line with a longitudinal strut 62 in the frame upstream portion. The upstream end of the longitudinal stitch begins where the valve skirt proximal end tapered portions contact one another. The tapered portions and the beginning of the longitudinal stitch 60 generally are positioned adjacent the junction between the upstream portion and the transition portion. The pieces of the valve skirt 33 and the valve skirt longitudinal stitch 60 can be positioned on the inner portion of the valve frame 20, not wrapped around the longitudinal strut 62. In some embodiments, the valve skirt longitudinal stitch 60 can wrap around the longitudinal strut 62.

The valve leaflets 56 are shown stitched to the valve skirt 33 between the adjacent skirt piece ends at the skirt longitudinal stitches 60. The commissural tabs 58 of two adjacent leaflet pieces extend through the longitudinal stitch 60. The two commissural tabs 58 are generally positioned in line with the longitudinal strut 62 and adjacent the foreshortening portion of the frame 20. The longitudinal strut 62 is located between the two radially outwardly protruding commissural tabs, as shown in FIG. 7A. The commissural tabs can be cut, or trimmed to size, to reduce the quantity of valve leaflet material wrapped around the longitudinal struts, as shown in FIG. 7B. The tabs can be wrapped around the longitudinal strut and then stitched together and around the longitudinal strut. In some embodiments, the commissural tabs can be the only portion of the valve body located on the outer surface of the valve frame. In some embodiments, the commissural tabs are stitched around the longitudinal strut and the longitudinal stitch 60 of the valve skirt is located at a different location. This can help minimize the size of the seam.

Figure 8:
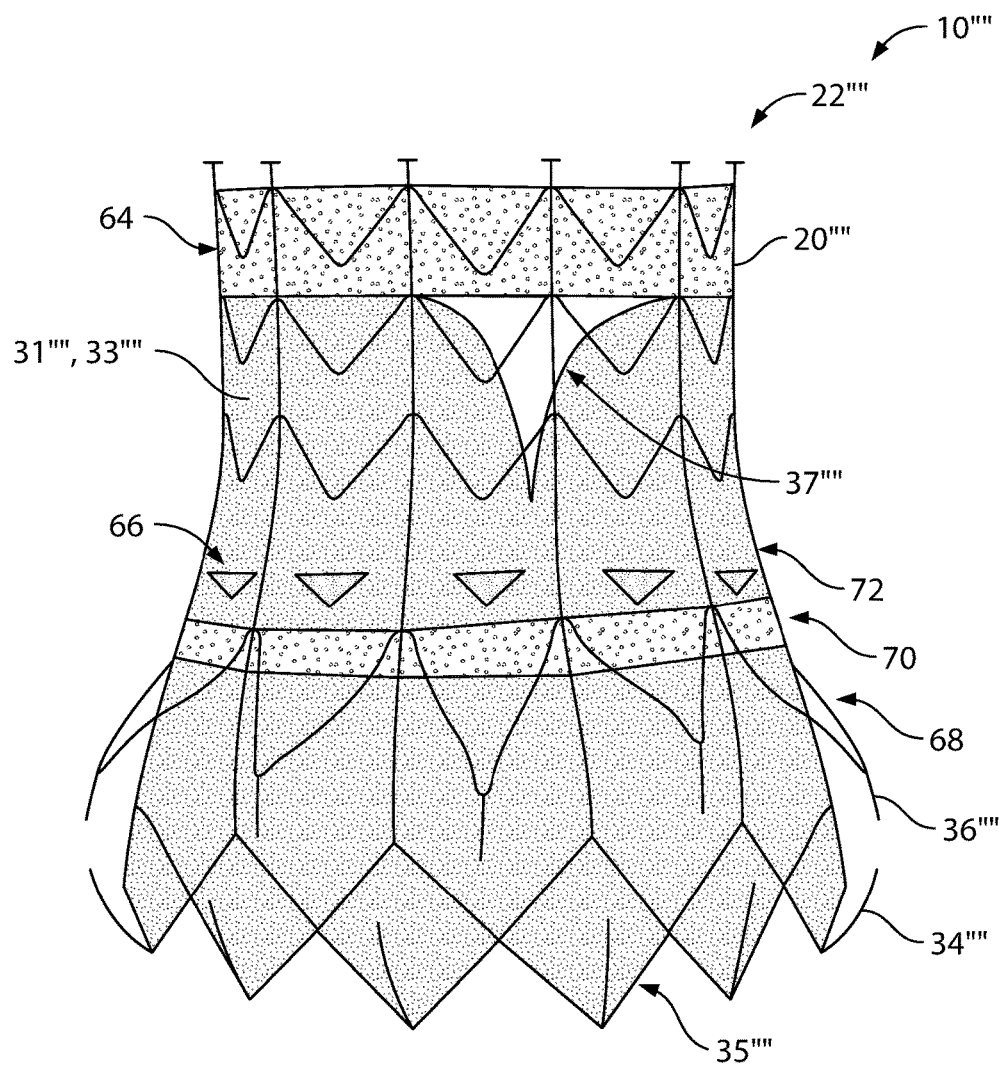
FIG. 8 is a schematic view of another embodiment of a replacement heart valve.

Turning now to FIG. 8, a schematic view of another embodiment of a replacement heart valve 10''' is shown. Numerical reference to components is the same as previously described, except that prime symbols ("") have been added to the reference. Where such references occur, it is to be understood that the components are the same or substantially similar to previously-described components. It should be understood that the illustrated heart valve implant includes each of the features designated by the numbers used herein. However, as emphasized repeatedly herein, these features need not be present in all embodiments.

The replacement heart valve illustrates various additional features, one or more of which may be incorporated into a respective replacement heart valve. Similar to the other replacement heart valves discussed herein, the replacement heart valve in FIG. 8 shows a valve skirt 33'''' having a scalloped proximal end 37''''. The valve skirt 33'''' may extend all the way to the proximal end of the valve frame or there may be a gap between the proximal end of the valve frame and the proximal end of the valve skirt.

In some embodiments, a support band 64 may be placed or positioned around or within the valve frame 20'''' at the proximal end 22''''. The support band 64 can be used to reinforce and/or constrain the valve frame at its proximal end 22''''. The support band 64 can help to control the expansion of the valve frame from the compacted to the expanded state and/or limit further expansion as previously discussed. The support band 64 can also be used to reduce the amount of motion that occurs at the proximal end 22'''' after the replacement heart valve 10'''' has been implanted within the mitral heart valve or other location.

In some embodiments, the support band 64 may comprise a fabric, polyester band. The support band may comprise a no-stretch or limited stretch material. Preferably the support band is not made of an elastic material or a material known to have high elasticity.

The support band 64 can be connected to the valve frame 20'''' with a plurality of stitches, loops, knots, or other types of connections. In some embodiments the support band 64 can sandwich the valve frame 20'''' between two sides or layers of the support band. Preferably, the support band is a single layer positioned within the valve frame and attached to the valve frame with a plurality of stitches around one or more of the longitudinal and/or undulating struts of the valve frame.

In some embodiments, a replacement heart valve 10'''' may include one or more flaps or gills 66 as illustrated in FIG. 8. The flaps or gills 66 can involve a cut or slit in the valve skirt material to allow for opening and closing the cut or slit. This can allow a small amount of blood to flow through the slit 66 and around the valve skirt 33''''. The flaps 66 can positioned anywhere on the valve skirt 33''''.

In the illustrated embodiment, a V-shaped cut 66 has been made in the valve skirt 33''''. The flap 66 is positioned within the valve frame 20'''' and as shown, can be considered as attached at the top or proximal end of the hole and hanging down into the valve. The flaps 66 can be attached at one or more sides of the hole. The flap 66 can include additional material so that the flap is larger than the hole made by the cut and can cover or close the entire hole. This additional material can also prevent the flap from being forced through the hole and effectively block or plug the hole.

The flaps or gills 66 in the valve skirt 33'''' can provide additional benefits. For example, one or more flaps 66 along the valve skirt can allow blood to flow around the valve skirt. The flaps 66 can also open and close with the flow of blood and the beating of the heart. For example, the flap 66 can be open during diastole and close during systole. The flaps 66 can reduce pressure on the valve skirt, while the primary flow of blood still flows through the center of the replacement heart valve and through the leaflets. In some embodiments, the flap 66 can be closed during diastole and open during systole. Further, in some embodiments, the flaps can be configured to allow some leakage, or a minimal amount of flow through when they are otherwise closed.

In some embodiments, the valve skirt includes the holes without the flaps. For example, the skirt can have one or more horizontal slits or slots. The slits can be positioned in the diamond or cell area of the frame, as one example. The valve skirt can also be a porous material. The valve skirt may or may not have a scalloped edge in this configuration. In some embodiments without a scalloped edge, or at least with some region of the skirt being upstream of the leaflet upstream edge, holes are formed only in the region of the skirt upstream of the leaflet upstream edge.

Another feature which can be included on a replacement heart valve 10'''' is a layered multi-piece valve skirt 33''''. The valve skirt 33'''' can have multiple pieces of material that overlap one another 68, 70, 72. This can allow blood to flow through the valve skirt 33'''' on the sides of the replacement heart valve 10'''' and between the layers 68, 70, 72 of valve skirt material. As shown, the proximal section of the valve skirt can be made up of one layer of material 72. A middle section of material 70 can be layered on top of the proximal section 72. The distal section 68 can then be layered over the end of the middle section 70. Similar to the flaps 66, blood can flow through the layers of valve skirt fabric. The layers can also be loose inside of the valve frame such that they act as a valve to open and close similar to the flaps discussed above, as shown in FIGS. 9A-9B.

The multi-piece valve skirt can be made of one or more materials. For example, the entire skirt, one or more layer, or one or more portions of one or more layers can be made of fabric, or of tissue, such as porcine tissue. In some embodiments, one or more layer can be a porous material, such as a porous fabric. The porous material can be configured to remain porous or to close up over time. For example, one layer such as either the layer 68, or the layer 72 can be made of fabric while the other two layers are made of tissue.

Figure 9A:
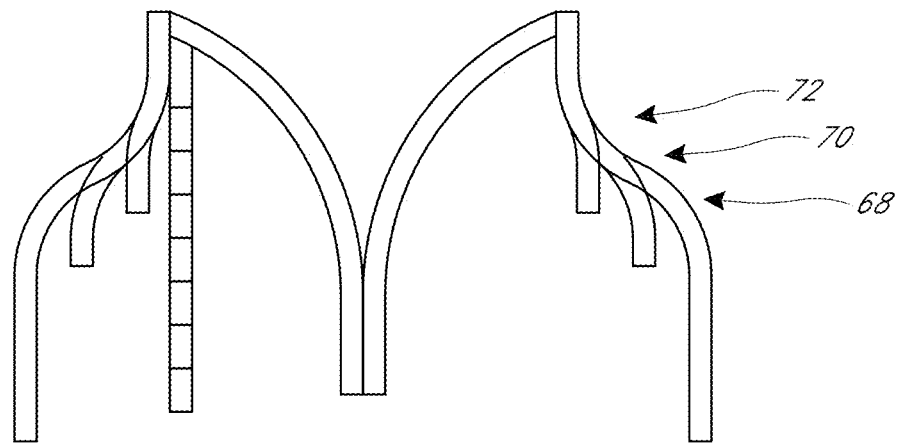
FIGS. 9A-9B are schematic views of another embodiment of a replacement heart valve.
Figure 9B:
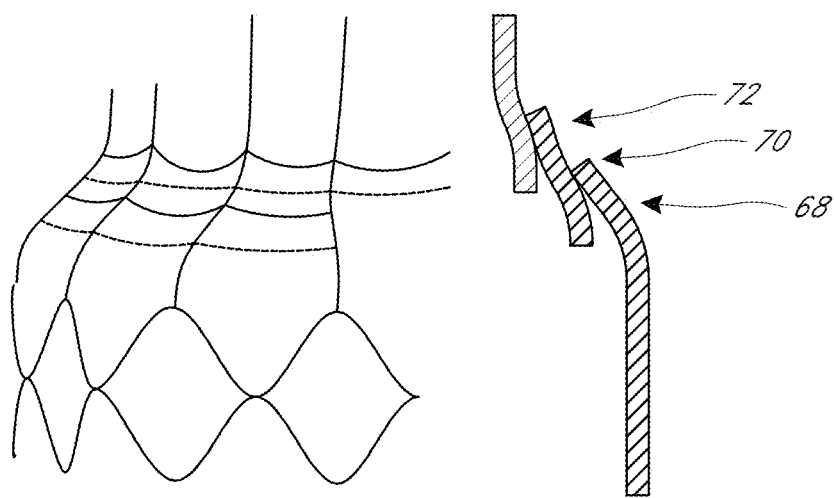

The multi-piece valve skirt can be sewn together at one or more locations. The stitch can be a discontinuous stitch that extends around the circumference and/or longitudinally. The gaps between the stitches and the overlapping material can be configured and sized to prevent prolapse. The multi-piece valve skirt can form one or more circular flaps as shown in FIGS. 9A-B. One end of the material can hang loosely within the valve. For example, a downstream end can hang loosely inside the valve as illustrated.

The overlapping multi-piece valve skirt, the scalloped edge, and the flaps can function as mini-leaflets to vent and/or allow flow through the replacement heart valve. The overlapping multi-piece valve skirt, the scalloped edge, and the flaps can also be beneficial during the implantation process to allow flow through the replacement heart valve prior to complete implantation of the device. These features and the related features discussed above can allow blood to flow other than directly through the valve. For example, a washout to the left atrium, a pop-off valve, a pressure relief valve, etc. can be provided. The holes, slits, flaps, overlapping, etc. can be configured to change over time, such that more flow is allowed through initially, but overtime the flow is diminished through tissue build-up or other effects of having the replacement valve in the body. In addition, holes, vents, slits, flaps, etc. can also be used to reduce pressure on the valve skirt when moving when the compressed and expanded positions.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. For example, the tether and eyelets of FIG. 2A and/or the reversed anchors of FIG. 4B can be used with any of the replacement heart valves of FIGS. 1, 5, and 8. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A replacement heart valve for deployment at a diseased native valve, the replacement heart valve comprising:
   an expandable frame configured to collapse radially to a first size for delivery and to expand radially to a second size upon deployment, the frame having an upstream end and a downstream end;
   a valve body positioned within the expandable frame, the valve body comprising a plurality of valve leaflets configured to permit blood flow in a downstream direction and to prevent blood flow in an upstream direction; and
   a material layer comprising one or more flaps positioned between the upstream and downstream ends of the frame along an exterior surface of the frame, each flap covering a corresponding opening in the replacement heart valve, wherein each flap is configured to allow blood to flow through the corresponding opening in a downstream direction when the frame is being expanded at the diseased native valve;
   wherein each flap is attached at an upstream end of the corresponding opening.

2. The replacement heart valve of claim 1, wherein the one or more flaps comprise a plurality of flaps positioned around a circumference of the replacement heart valve that cover a plurality of the corresponding opening.

3. The replacement heart valve of claim 1, wherein the one or more flaps are configured to allow blood to flow through the corresponding openings from a location external the replacement valve to a location internal to the replacement valve.

4. The replacement heart valve of claim 3, wherein the location internal to the replacement valve is downstream of the plurality of valve leaflets.

5. The replacement heart valve of claim 1, wherein the exterior surface of the frame is configurable to have an at least partially conical shape to facilitate blood to flow through the corresponding openings.

6. The replacement heart valve of claim 1, wherein each of the valve leaflets has a scalloped, upstream edge.

7. The replacement heart valve of claim 6, wherein the one or more flaps are located downstream of the scalloped, upstream edges of the valve leaflets.

8. The replacement heart valve of claim 1, wherein the corresponding openings are located upstream of an upstream side of the valve leaflets.

9. A replacement heart valve for deployment at a diseased native valve, the replacement heart valve comprising:
   an expandable frame comprising a proximal end and a distal end, the frame configured to radially expand and collapse for deployment at the diseased native valve, wherein the frame comprises a plurality of struts defining a plurality of cells;
   a valve body comprising a plurality of valve leaflets, wherein each of the valve leaflets extends between a fixed proximal edge and a free distal edge, the free distal edges configured to open to allow flow in a first direction from the frame proximal end to the frame distal end and configured to alternatively close to prevent flow in a second direction from the frame distal end to the frame proximal end; and a valve skirt attached to the expandable frame covering one or more of the cells of the frame, wherein the valve skirt defines one or more openings that are sized and configured to promote blood flow through the one or more openings, wherein the one or more openings are located proximally of the proximal edge of the valve leaflets; and one or more flaps formed from a layer of material, each flap covering a corresponding one of the one or more openings defined by the valve skirt, wherein the one or more flaps are configured to allow blood to flow through the one or more openings in substantially one direction.

10. The replacement heart valve of claim 9, wherein the one or more openings are sized and configured to promote blood flow in substantially the second direction.

11. The replacement heart valve of claim 9, wherein the one or more openings are sized and configured to allow blood flow in the first direction.

12. A replacement heart valve for deployment at a diseased native valve, the replacement heart valve comprising:

an expandable frame comprising a proximal end and a distal end, the frame configured to radially expand and collapse for deployment at the diseased native valve, wherein the frame comprises a plurality of struts defining a plurality of cells;

a valve body comprising a plurality of valve leaflets, wherein each of the valve leaflets extends between a fixed proximal edge and a free distal edge, the free distal edges configured to open to allow flow in a first direction from the frame proximal end to the frame distal end and configured to alternatively close to prevent flow in a second direction from the frame distal end to the frame proximal end; and a valve skirt attached to the frame covering one or more of the cells of the frame, wherein:

valve skirt comprises multiple layers of material that overlap one another, and the valve skirt defines one or more openings that are sized and configured to promote blood flow through one or more cells of the frame covered by the valve skirt in the first direction, the one or more openings defined between the layers to allow blood to flow through the layers.

13. The replacement heart valve of claim 12, wherein the one or more openings are located at a portion of the frame configurable into a conical shape.

14. The replacement heart valve of claim 12, wherein each of the valve leaflets has a scalloped proximal edge.

15. The replacement heart valve of claim 14, wherein the one or more openings are located distal of the scalloped proximal edges of the valve leaflets.

16. The replacement heart valve of claim 12, wherein the plurality of valve leaflets are attached to the valve skirt.

17. The replacement heart valve of claim 12, wherein the one or more openings are located proximally of the proximal edge of the valve leaflets.

* * * * *